United States Patent
Franke et al.

(10) Patent No.: US 12,285,601 B2
(45) Date of Patent: Apr. 29, 2025

(54) EX VIVO METHOD OF MANUFACTURING A WIRE STRUCTURE ELECTRODE

(71) Applicant: NEURONOFF, INC., Cleveland, OH (US)

(72) Inventors: Manfred Franke, Cleveland, OH (US); Shaher Ahmad, Cleveland, OH (US); Stephan Nieuwoudt, Cleveland, OH (US); Amelia Howe, Cleveland, OH (US); Aniruddha Upadhye, Cleveland Heights, OH (US); Emily Szabo, Strongsville, OH (US); Derrick Liu, Hudson, OH (US); Sean Zuckermann, Lakewood, OH (US); Craig Watson, Cleveland Heights, OH (US)

(73) Assignee: Neuronoff, Inc., Cleveland, OH (US)

( * ) Notice: Subject to any disclaimer, the term of this patent is extended or adjusted under 35 U.S.C. 154(b) by 412 days.

(21) Appl. No.: 17/778,373

(22) PCT Filed: Nov. 19, 2020

(86) PCT No.: PCT/US2020/061374
§ 371 (c)(1),
(2) Date: May 19, 2022

(87) PCT Pub. No.: WO2021/102195
PCT Pub. Date: May 27, 2021

(65) Prior Publication Data
US 2023/0024284 A1    Jan. 26, 2023

Related U.S. Application Data

(60) Provisional application No. 62/937,673, filed on Nov. 19, 2019, provisional application No. 62/965,047, (Continued)

(51) Int. Cl.
*H01S 4/00* (2006.01)
*A61N 1/05* (2006.01)
(Continued)

(52) U.S. Cl.
CPC ....... *A61N 1/0504* (2013.01); *A61N 1/37205* (2013.01); *A61N 1/3787* (2013.01)

(58) Field of Classification Search
CPC ...... A61N 1/0456; A61N 1/05; A61N 1/0504; A61N 1/3605; A61N 1/37205; A61N 1/3787
See application file for complete search history.

(56) References Cited

U.S. PATENT DOCUMENTS

| | | | | |
|---|---|---|---|---|
| 5,224,491 A | * | 7/1993 | Mehra | A61N 1/0565 607/126 |
| 5,925,054 A | * | 7/1999 | Taylor | A61B 17/1219 606/191 |

(Continued)

*Primary Examiner* — Paul D Kim
(74) *Attorney, Agent, or Firm* — Joel Douglas; Thomas Ciesco; Jeffrey E. Semprebon

(57) ABSTRACT

An injectable wire structure electrode can assimilate with surrounding tissues after injection, inducing in-growth of blood vessels, collagen and other tissue. Assimilation secures the electrode to the tissue without sutures and prevents relative motion which can lead to inflammation and scarring. Associated methods of manufacturing and injection are disclosed, as well as systems including a dermal multiplexer for power delivery.

3 Claims, 42 Drawing Sheets

Related U.S. Application Data filed on Jan. 23, 2020, provisional application No. 63/079,275, filed on Sep. 16, 2020.

(51) Int. Cl.
*A61N 1/372* (2006.01)
*A61N 1/378* (2006.01)

(56) References Cited

U.S. PATENT DOCUMENTS

| | | | | |
|---|---|---|---|---|
| 2008/0262584 A1* | 10/2008 | Bottomley | ........... | A61N 1/0488 |
| | | | | 29/605 |
| 2009/0200890 A1* | 8/2009 | Halstead | ............ | H02K 15/0464 |
| | | | | 29/596 |

* cited by examiner

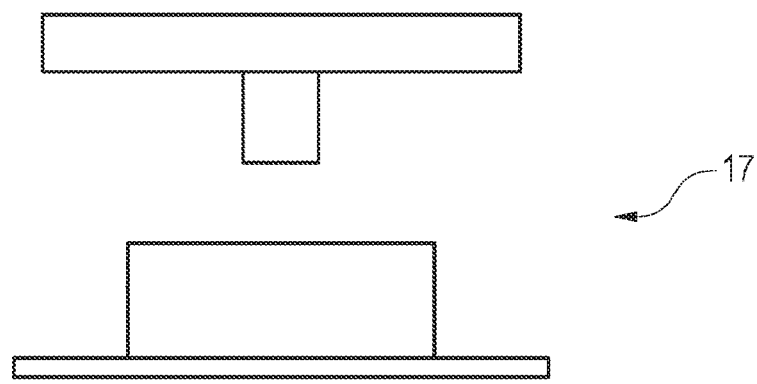
FIG. 16-a
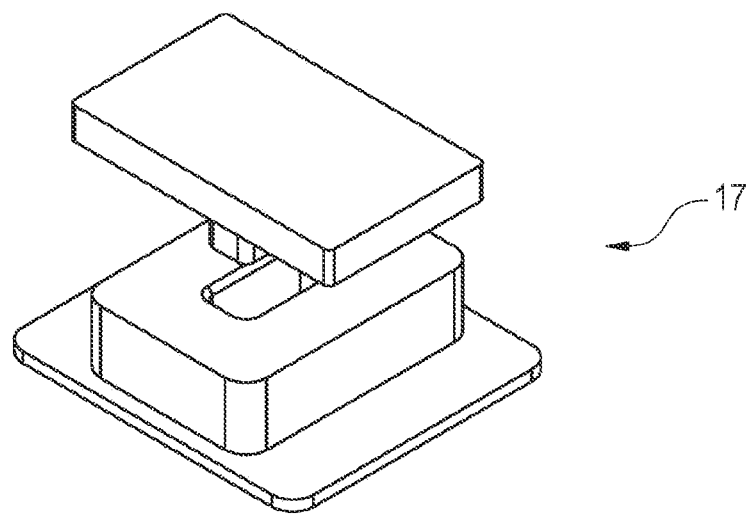
FIG. 16-b

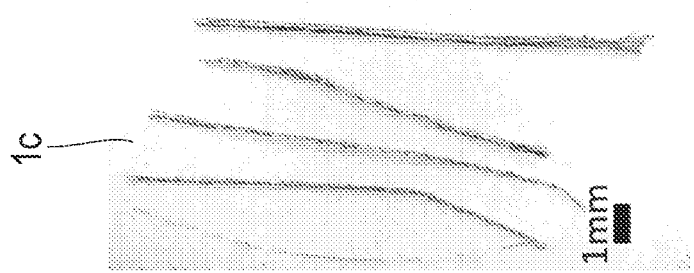
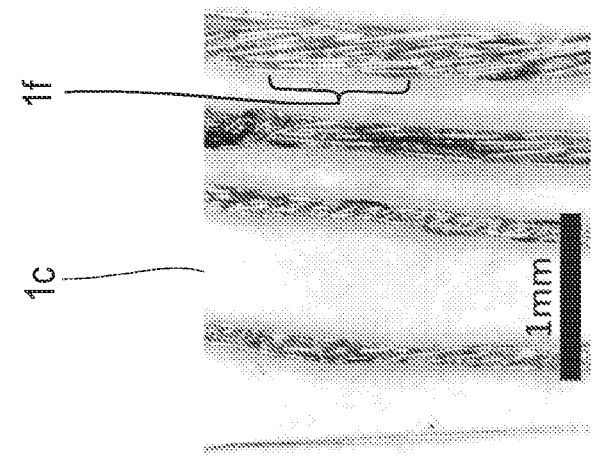
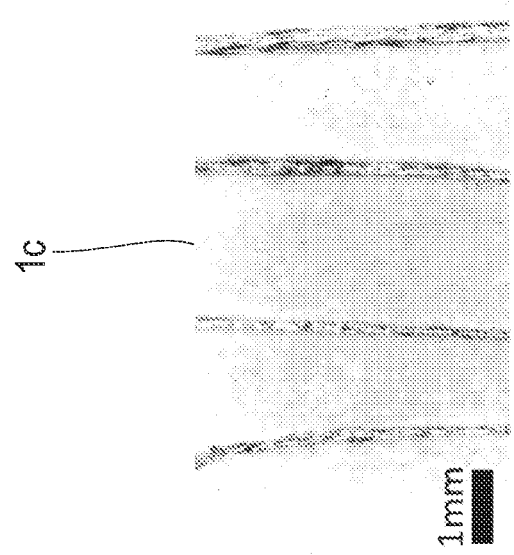
FIG 20(C)
FIG 20(b)
FIG 20(a)

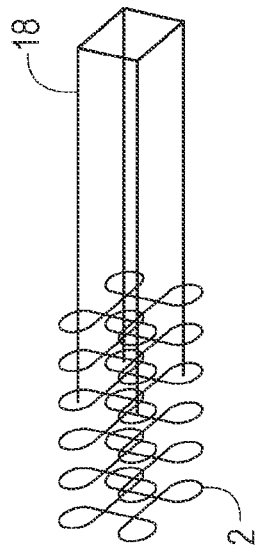
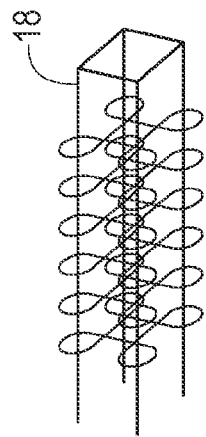
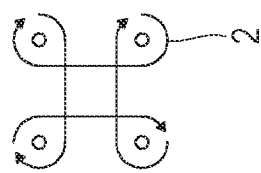
FIG. 21(a)
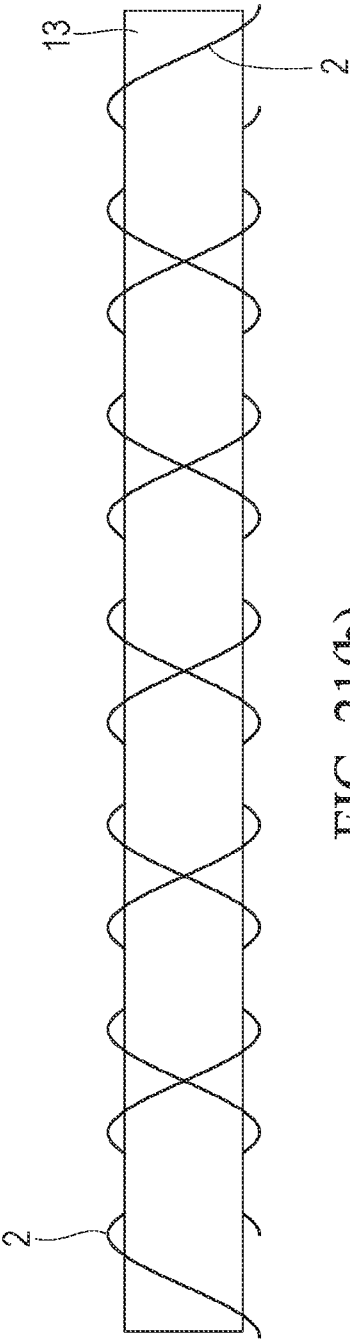
FIG. 21(b)

Pre-Implant

Post-Implant

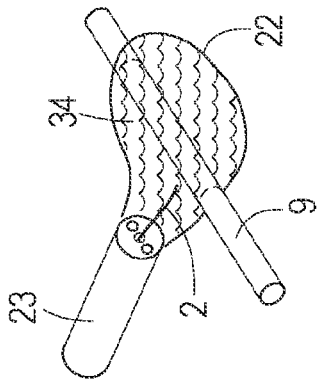
FIG. 31(a)
FIG. 31(b)
FIG. 31(c)
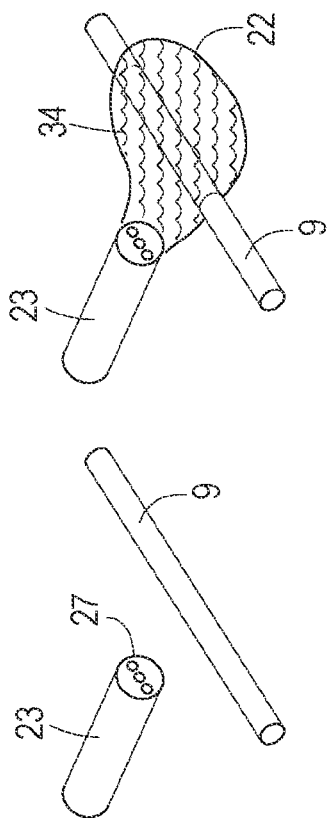
FIG. 31(d)
FIG. 31(e)
FIG. 31(f)

EX VIVO METHOD OF MANUFACTURING A WIRE STRUCTURE ELECTRODE

CROSS-REFERENCE TO RELATED APPLICATIONS

This application is a National Phase entry of International Application PCT/US2020/061374, and claims priority to, and the full benefit of the following: U.S. provisional patent application No. 62/937,673 filed on Nov. 19, 2019; U.S. provisional patent application No. 62/965,047 filed on Jan. 23, 2020; and U.S. provisional patent application No. 63/079,275 filed on Sep. 16, 2020.

FIELD OF THE INVENTION

The invention relates to electrodes that are designed and configured to transmit energy within the body.

BACKGROUND

The side effects of pharmaceuticals can be numerous, and sometimes as bad as the condition for the relief being sought, such as opioid addiction suffered by some chronic pain victims. Surgical intervention can be both traumatic and generally more expensive than pharmaceuticals to deliver because of the requirement of operating rooms and the sophisticated machines and people required for major surgery, although systemic side effects from surgery are not as much of a threat as from pharmaceuticals. The recovery from surgery can also be a major hurdle for many patients because of open cut downs. Physicians currently have options for implantable devices to interface with nerve and other target tissue, but often the implantation surgery through open cut downs can be as traumatic as general surgical interventions. Electrodes which are injectable through a needle and connected to a power source combine the best of all of the above: efficacy at a specific location, lack of systemic side effects and minimally invasive placement.

There have been minimally invasive techniques proposed previously which involved micron-sized conductive particles mixed into a flowable and curable glue which cures and reaches its final configuration inside the body. Issues with the particle-based design though include some lack of control over the flowing of the glue before it cures and also the possibility that, after the body's immune defenses and fibrous tissue intervene, the particles can dissipate or be moved, reducing efficacy and/or also threatening potential removal.

SUMMARY

An injectable wire structure electrode can be designed and configured to transmit energy within the body at a higher conductivity for this energy than for surrounding tissues and to achieve a change in metabolic activity or structure in the tissue contacted on at least one end of the wire structure. The injectable wire structure electrode as disclosed herein, with the associated methods for manufacturing and placement, is a novel approach to interfacing with nerve and other target tissue to deliver therapy which can be highly local and also, depending on the target tissue, systemic and affecting the body as a whole.

An ex vivo method of manufacturing a wire structure electrode for implantation injection near a tissue target inside a body can comprise the steps of providing at least one highly conductive wire, wrapping such wire(s) around at least one mandrel outside the body to produce spools comprising two ends, and compacting the spools to form a wire structure not exceeding 3 mm in diameter having voids and a roughened and porous surface.

The particle-based approach discussed above has been advanced in U.S. patent application Ser. Nos. 16/439,323 and 16/620,499 and related applications by some of the present inventors, and it has a field of utility, but an injectable wire structure electrode solves the problem of potential dispersion of particles leading to reduced efficacy and/or inability to accomplish full removal. The wire structure electrode, created from at least one highly conductive wire which is spooled, flattened, rolled, compacted, twisted or braided, has vastly more mechanical strength than the particle based electrode, which is held together only by the curable liquid until it is resorbed or pushed by the movements, or by fibrotic tissues of the body.

The injectable electrode disclosed herein maintains the injectability of the prior micron-sized particle-based approach but instead comprises at least one ultra thin wire which can be many meters in length which is, through various methods described herein, compacted into a volume small enough to be injected through a needle. This wire structure electrode is highly conductive for a given form energy and maintains its general mechanical shape, although it may be flexible, bendable, stretchable and deformable in pre-determined ways, thus minimizing the less predictable particle solution and the irritation of bodily tissues, and likewise thickness of encapsulation resulting from irritating bodily tissues resulting from any of the many current implantable electrodes which are quite rigid. The wire electrode may comprise overlapping loops and folds of wire, to create a highly conductive pathway for transmission of energy. The flexibility of the wire structure electrode allows the physician, under fluoroscopy, ultrasound or other non-invasive or minimally invasive visualization, to inject it in a number of shapes and orientations, and bend, bunch and shape it according to the particular target tissue shape and desired surgical access angles. Although the wire structure electrode can be dense and has high charge injection capacity because of the high surface area, in many embodiments it is not entirely solid and maintains voids or empty spaces into which additional agents can be intermingled to provide various materials to provide benefits.

Furthermore, as the wire structure electrode can be variably dense, based on the amount of wire deployed (amount measured in length and diameter to define a volume and a surface area of the total wire within the final volume at the tissue interfacing location), the wire structure electrode offers an intrinsically high charge injection capacity because of the high surface area of the wire chemically exposed to the surrounding electrolyte within the living body. The charge injection capacity may be varied, by several methods, by increasing the wire length and decreasing the wire diameter of the wire or wires used to form the wire structure electrode while retaining the overall volume of the wire structure electrode constant. The entire inside volume of the wire structure electrode likewise may contribute to the charge injection during a deposition of electrical energy, the surface area of the wire on the inside of its bulk shape and the roughened and porous surface of the bulk shape of the wire structure electrode not being prevented in its ability to inject charge by bodily proteins and what is commonly referred to as biofouling. As a result, the wire structure electrode is able to retain its ability to inject large amounts of charge over extended periods of time with acute and chronic placements (for months and years) offering significant advantages over the current state of the art of electrodes.

Additional benefits over current electrodes include a high degree of biocompatibility including observed in-growth of blood vessels and other tissue which demonstrates the body does not attack the wire electrode as manufactured and injected as disclosed herein. In turn, the in-growth of blood vessels and other tissue also serves to anchor the wire electrode without the need for sutures, clamps or cuffs often required with current electrodes. A closely related benefit is that the wire structure electrode lends itself to either no or very light fibrotic capsule, which allows the wire structure electrode to communicate energy with no or little impediment. This ability of the body to assimilate the wire structure electrode is also one of its advantages. Merely implanting a wire structure without the construction and methods of injection and associated components and techniques described herein would not result in the biocompatibility of the wire structure electrode disclosed herein.

As described herein in greater detail, the injectable wire structure electrode combines high charge injection capacity, porosity, flexibility, stretchability, deformability, biocompatibility, assimilability as well as the obvious benefits of minimally invasive implant and explant.

BRIEF DESCRIPTION OF THE FIGURES

FIG. 8 (b) is similar, except the rolled wire structure here has an embedded guidewire and the plunger comprises an opening for the guidewire. FIG. 8 (c) shows the rolled wire structure with a guide wire in a "J" position at the tissue target.

FIGS. 15A(a)-(c) are photographs of a set up testing impedance in folded wire structure implanted subcutaneously.

FIGS. 16 (a) and (b) are respectively a side view and a perspective view of one embodiment of a mold for compacting a folded wire structure.

FIG. 19A shows images of folded wire structure electrodes ready to inject, as well as a novel fixture for adapting insertion to any syringe.

FIGS. 20 (a)-(c) are images of twisted or braided strands of gold wire, with number of strands left to right being 1, 6, 10, 20 and 40: FIG. 20(a) closest, FIG. 20(b) next closest, and FIG. 20(c) farthest views.

FIG. 21 (a) depicts patterns of wrapping wire around a rectangular structure which may comprise dissolvable material or a thermoplastic to be heated to allow the wrapped wire to collapse; and FIG. 21(b) depicts wrapping at least two wires of different diameter around a single mandrel, each wire out of phase with the other.

FIG. 23 (b) shows the same embodiment as in FIG. 23 (a), but the central portion which is of lower compaction ration allows the electrode to bend reliably and predictably at this location.

FIGS. 31(a)-31(f) steps of injection of one embodiment of a cannula using fluid as dissection means to extrude an injectable wire electrode, employing creation of a cavity first for the wire near the tissue target: FIG. 31(a) insertion end approaches the tissue target, FIG. 31(b) dissection with a fluid such as saline solution from the dissection port creating a cavity near the tissue target, FIG. 31(c) wire extrusion starts from the wire port into the cavity, FIG. 31(d) wire meanders within the cavity, FIG. 31(e) cavity filled with wire, FIG. 31(f) tip has been retracted and the arrow points toward continuation of wire extrusion towards the subcutaneous region for connection to power delivery (not shown).

FIG. 32(a) approach target nerve with delivery probe, FIG. 32(b) deploy balloon, FIG. 32(c) full deployment of balloon for blunt dissection of cavity above nerve. FIG. 32(d) retraction of balloon and filling of balloon formed cavity with saline, FIG. 32(e) injection of wire, FIG. 32(f) cavity filling with wire, FIG. 32(g) dissected cavity fully filled with wire, FIG. 32(h) retraction of probe and continuous wire deposition/delivery, and FIG. 32(i) encapsulated injectable wire electrode with arrow pointing to subcutaneous region where this process is repeated.

DETAILED DESCRIPTION

Figure 1:
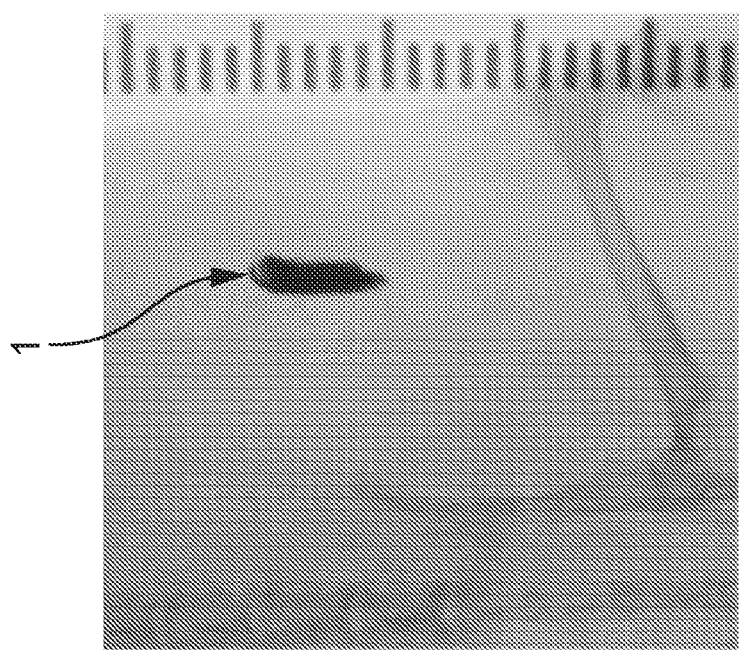
FIG. 1 is an image from ultrasound visualization of a folded wire structure located subcutaneously in the vicinity of an animal's sciatic nerve.

Highly Conductive Wires
a. Material

In one embodiment, the highly conductive wire 2 used to manufacture the electrode herein is gold bonding wire which has been used in packaging techniques in the manufacture of computers, that is, in connecting components in computers. In one embodiment, a suitable gold bonding wire is the A-14 type manufactured by Heraeus Electronics of Hanau, Germany, and which is available in a range of diameter from 18-33 microns. A-14 has an advantage in that it is 99.99% pure gold wire. A 25 micron diameter gold bonding wire of this sort is suitable in numerous embodiments of the wire structure electrode. Additionally, gold bonding wire of a 100 micron diameter is suitable, and the range overall is approximately 2 to 300 microns in diameter. The wire structure electrode may comprise gold wire as well as other conductive wires selected from the group consisting of gold, silver, platinum, stainless steel, titanium, titanium-nickel, iridium, platinum-iridium, tungsten and other metal alloys such as MP35N, a cobalt-nickel-chromium alloy with molybdenum added for corrosion resistance. Wires comprising the above metals are readily available commercially in the 2-300 micron diameter range, and wires of other diameters are also suitable for embodiments of the wire structure electrode. The final material and diameter selection for a particular embodiment is dependent on patient biocompatibility and desired tensile (mechanical) and electrical properties for the particular application and embodiment, as well as dependent on optimum force supplied by the wire structure electrode onto the tissues against which it is pressed, because mechanical forces from any implanted electrode influence formation of encapsulation tissue.

Wires of these biocompatible metals have different mechanical and electrical properties, such as conductivity, and the potential effects for heating of the wires during the conduction of electrical current. The metal composition of the wires can be varied to introduce desired physical properties.

b. Surface Modification for Wires

The surface of the wire may be modified to enhance electrochemical and/or mechanical properties. The wire surface may be modified via galvanic deposition (GD) or physical vapor deposition (PVD, such as sputtering) or chemical vapor deposition (CVP) of metals selected from the group consisting of gold, silver, platinum, stainless steel, titanium, titanium-nickel, iridium, platinum-iridium, tungsten and other metal alloys including without limitation MP35N. The surface of the wire may further be modified to include non-metallic surface treatments such as PDOT deposition to enhance the electrochemical interface properties of the nests.

In several embodiments, the wire surface electrodes to be implanted are manufactured by either (1) forming the wire into a rolled 1a, folded 1b, twisted or braided 1c or extruded 1j structure and then modifying the surface via e.g. PVD, CVD, GD or other means, or (2) first modifying the surface of the wire itself via e.g. PVD, CVD, GD or other means, and then forming the wire into a wire structure electrode.

While mass-producing wires with modified surfaces has its advantages in mass production, there are draw-backs in the mechanical integrity of the surface modification if it is subjected to the bending and twisting that occurs during the formation of a wire structure electrode.

Stainless steel wires, coated with a more conductive metal (e.g., gold) by means such as PVD or electroplating allows for the wire electrode to be of similar tensile strength and ability to resist breaking under bending as the core material, all the while allowing the current to take the skin of gold as the primary conductive path.

Yet another path to forming a wire structure electrode from different wire base materials for a combination of enhanced electrical and mechanical capabilities is the gold coating of stainless steel wires by the means of CVD, PVD or other means as mentioned before, prior to combining the surface-treated steel wires with pure gold wires that offer lesser mechanical strength than the stainless steel wires but significantly higher conductivities for electrical current at larger gold cross sections than the surface-treated stainless steel wires. The two wires, the gold coated stainless steel and the pure gold wires may then be jointly deformed mechanically by the means of winding, twisting, folding, spooling up or other means of mechanically forming the wire structure electrode.

c. Aspect Ratio

The aspect ratio of the wires used to form the injectable wire electrode are very high, much higher than any currently available electrode. For examples, a 25 micron diameter wire which is 25 meters long would have an aspect ratio of 1,000,000:1, and a similar diameter wire 10 meters long would have an aspect ratio exceeding 400,000:1.

d. Combinations of Differing Materials, and Other Materials

Figure 2:
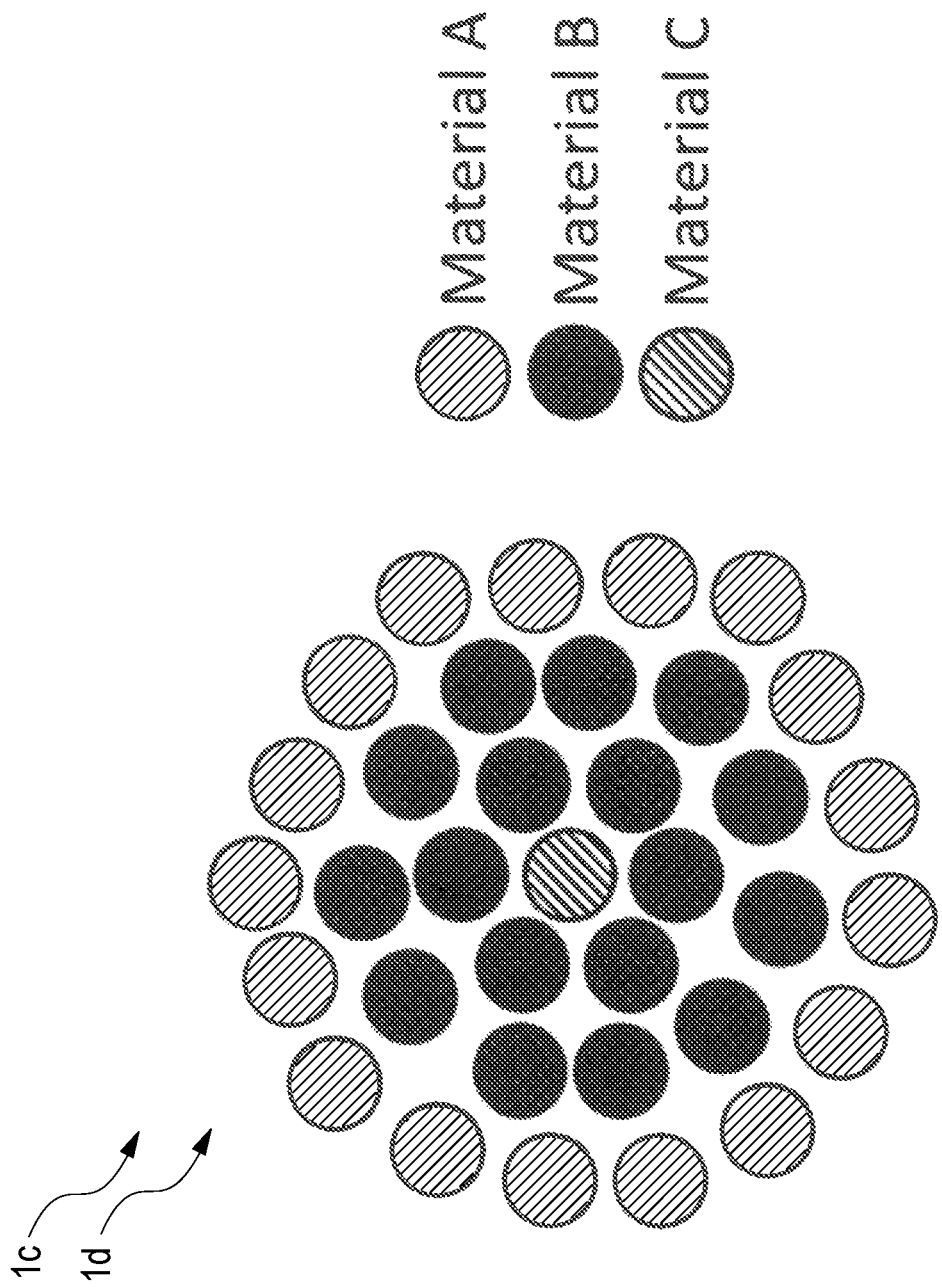
FIG. 2 is a schematic of a cross-section of differing wires and other material strands, shown by the black, striped and dot matrix fill circles.

A combination wire structure electrode 1d may be manufactured from a highly conductive wire 2 such as gold and other materials in a blended fashion, as shown in FIG. 2, which is a schematic of a cross-section of differing wires and other material strands, shown by the black, striped and dot matrix fill circles. In the example embodiment shown, which is a rope-like structure, the dot matrix circles are a nonconductive material such as silk for mechanical modification and additional flexibility, the black circles are gold wires and the striped circle is a stainless steel core. In one embodiment, these components are then twisted into a rope-like structure. The constituent components of this rope-like wire structure can be selected for the following properties: conductivity, flexibility, strength, biological response, radio-opacity and elution of pharmacological, immunological, hemostatic and/or angiogenic agents. This particular pattern is merely one example and many patterns and numbers of wires and other material strands are potentially useful. In FIG. 2, the differing wires and/or materials are show in the pattern in which they are fed together from multiple spools. After the wires and/or materials are brought into close proximity, they are twisted to secure them together into a combination wire structure electrode 1d which is also a twisted or braided wire structure 1c which is rope-like.

e. Advantages of Thinner Vs. Thicker Wires

Thinner wires (e.g., 25 micron gold bonding wire) are more flexible and may require less volume when processed into any wire structure electrode 1 herein, whose outer diameter in some embodiments is 1 to 2 mm.

Thicker wires (larger diameter wires such as 100 micron gold bonding wire) are less flexible and may require more volume when processed into any wire structure electrode 1 but offer higher stiffness in appropriate applications in the body.

Figure 3:
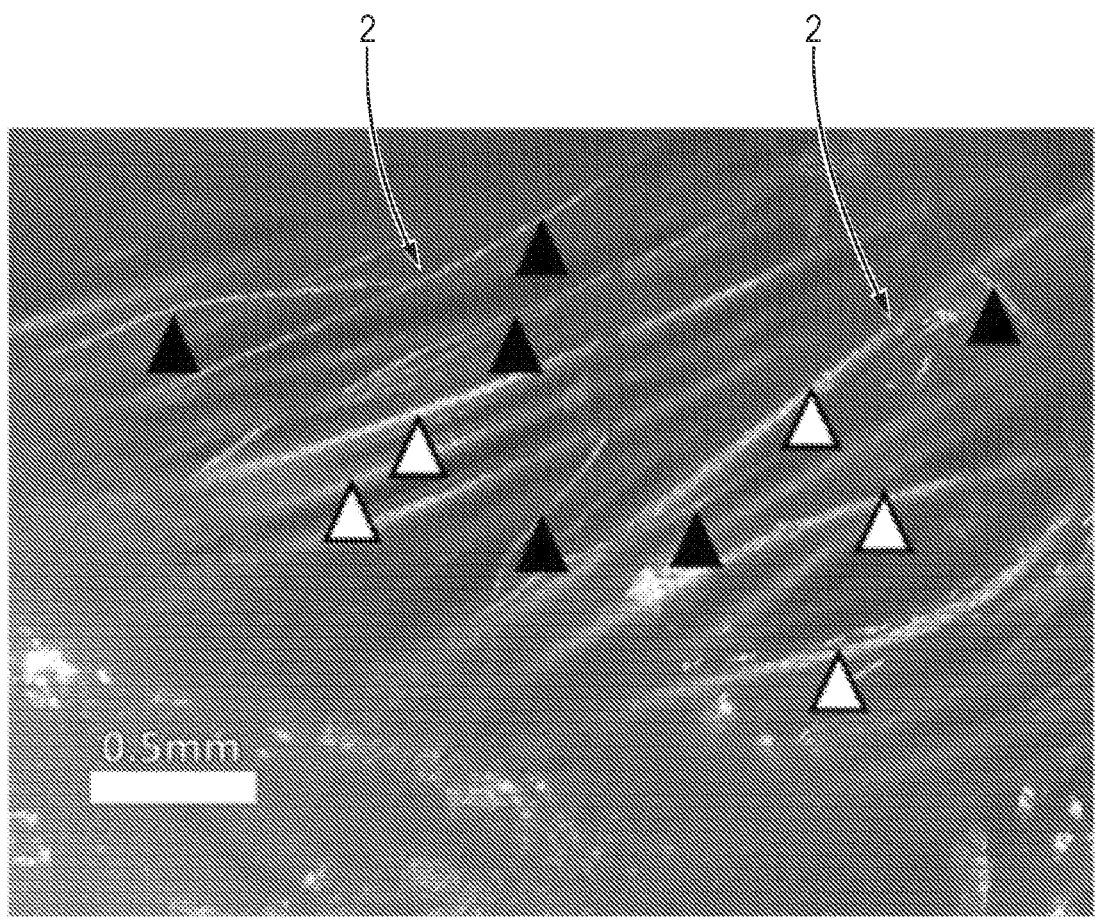
FIG. 3 is a photograph of an explanted folded wire structure comprising gold wire in a preclinical rodent model, which is a combination of 100 µm and 25 um wire at a 1:1 length ratio. Filled triangles indicate 25 um wire interwoven with the 100 um wire indicated by empty triangles.

Combining thinner with thicker wires during the manufacturing process allows for a mixture of mechanical capabilities. Embodiments of the wire structure electrode combining 25 micron and 100 micron gold wire at varying ratios had higher stiffness than those limited to 25 micron gold bonding wire, but were still more flexible than those of the same bulk shape 1k entirely made of 100 micron gold bonding wire structure electrodes. The bulk shape 1k of the wire structure electrode has a porous surface 1f. FIG. 3 is a photograph of an explanted gold folded wire structure in a preclinical rodent model. Combination of 100 micron and 25 micron wire at a 1:1 length ratio. Filled triangles indicate 25 micron wire interwoven with the 100 micron wire indicated by empty triangles.

More mechanical stiffness may be important for (1) the injection procedure when the wire structure must pass through the delivery needle, then fill the formerly created volume void inside the tissue, as well as (2) the modification for the mechanical requirements presented by the biological tissue, such as nerves that are susceptible to pressure applied and may respond with pressure damage if not accounted for.

Larger peripheral nerves can withstand larger lateral and coaxial forces than smaller, and/or thinner nerves that have a smaller perineurium and epineurium, both of which can aid with the cushioning of mechanical forces applied on the outside of a nerve and applied to a nerve.

There is a correlation between placing a smaller diameter (e.g., 25 micron) wire structure electrode into live biological tissue chronically (e.g. 4, 8, 16 or up to 26 weeks) and a reduction in inflammation covering the outside of the electrode compared to larger diameter wire. Smaller wire diameters in rolled or folded wire structures are not only more flexible than larger diameters, but they likewise result in thinner encapsulation of the wire electrode because reduced stiffness produces less irritation.

Smaller diameter wire based electrodes are more advisable for more delicate tissues, such as thin peripheral nerves (e.g. less than 2 mm in outer diameter, especially nerves of 0.1 to 1 mm in diameter). Likewise, nerves of large diameter of up to 1 cm and more (i.e. the sciatic nerve being in certain dimensions up to about an inch in thickness) are more forgiving to mechanical forces applied by the wire structure electrode and thus can be supplied with, for example, a 100 micron diameter wire structure electrode. Last but not least, when both capabilities are required of the wire structure, high mechanical shear and tensile strength combined with minimal mechanical interference with the target or other surrounding tissues, then combinations of different diameter wires achieve the desired effect.

Yet another aspect of combining larger diameter wires with thinner wires is the tendency for the larger wires to transport electrical current preferentially along the wires instead of injecting it into the electrolyte as the ratio of the wire's cross-section to wire surface area changes when a wire diameter is increased. The wire cross-sectional area increases quadratically, meaning the impedance falls off with a square as the diameter increases, while the wire's outer surface area only increases linearly. This change in ratio causes larger diameter wires to more preferentially conduct electrical current while physically located in a dielectric electrolyte such as bodily fluids, while thinner diameter wires possess the tendency to transfer, or inject, more current into the surface boundary to the dielectric electrolyte in comparison to the amount of current transported along the thin wire itself.

Preferential transport of current through thicker wires along with preferential injection current from thinner wires permits wire structures with wires of different thicknesses to provide sections that are preferentially functioning as (1) interface region to pick up electrical currents, (2) transport region to move up electrical currents along the wire structure, and (3) interface region to re-emit electrical currents into the electrolyte surrounding the cells of the target interfacing tissue. Note that the entire structure, in one embodiment, is manufactured from only one material, 99.99% gold or stainless steel, offering the electrochemical advantages and process cost savings.

The Wire Structure Electrode a. Geometry: Folded, Rolled and Rope-Like

Different embodiments of the wire structure electrode include without limitation a "folded wire structure," "rolled wire structure," a "wrapped wire structure," a "twisted or braided wire structure," and a "combination wire structure."

b. Biocompatibility and Assimilation by the Body

One of the main challenges for implanted electrodes is to avoid provoking an attack by the body's natural defenses against foreign objects. A significant problem and challenge of current electrodes which include smooth lead wires is called "pistoning." This refers to the movement of a smooth wire or other structure (insulated or uninsulated) within a fibrotic capsule. That is, a smooth surface is prone to separate from fibrotic tissue during the body's normal movements because the fibrotic tissues, in essence, has difficulty holding on to the smooth surface, so the foreign object, even a smooth surface, will rub against the fibrotic tissue repeatedly. This movement, or pistoning, leads to irritation of the fibrotic capsule which produces a capsule of even greater thickness, and this leads to greater inflammatory responses which can inhibit electrical current flow to the tissue intended to receive the current or other energy.

One of the advances of the present wire structure electrode is the elimination or reduction of pistoning. The wire structure electrode may comprise overlapping loops and voids in a bulk shape comprising a roughened and porous surface, and loops protruding from said roughened and porous surface of said bulk shape. The roughened and porous surface contacts the surrounding tissue directly, and the interlocking of the roughened and porous surface means that a fibrotic layer will actually be attached more closely to the wire structure electrode rather than to smooth surfaces, and greatly reduce relative movement of the electrode and the fibrotic layers, and thus the potential for inflammation.

The porous surface also allows in-growth of blood vessels and collagen fibers as a process of the body's assimilation with the wire structure electrode. The wire structure therefore integrates with the surrounding living tissue when placed into a living body, allowing the living body to grow cells within the bulk shape of the wire electrode, including the formation of blood vessels and other vessels and cell layers supporting the healthy symbiosis of metallic components of the wire electrode and the bodily cells and tissues grown over time. This assimilation also means when the wire structure undergoes mechanical deformation when subjected to stress and strain within the body with the potential of cells and tissues temporarily separating from the metallic components of the wire electrode, the surrounding tissue may then be repaired by the body via the formation of new cells and tissues, reattaching the formerly connected cells and tissues to the metallic components of the wire structure, reestablishing the bio-mechanical interface to allow chronic long term stability of energy conduction by and through the components of the wire structure to the target tissues.

Assimilation also allows the cells and tissues to treat an inflammation caused by, for example, any outside force (e.g. knife, needle, blunt force) by providing white blood cells, t-cells and other immune cells to attack any invading biological and non-biological threats that may be brought into or near the wire structure. The tissue-supporting structures such as small blood vessels aid the bodily response to inflammation in or near the wire structure.

Assimilation includes the mechanical integration of the wire structure electrode with a partial or full digestion of the object, leading to a mechanical improvement of the interface between the wire structure and surrounding tissue. Assimilation also includes the mechanical reshaping of the wire structure which may, in addition to having a smaller and a larger dimension, show signs of taking on the small local changes in shape such as grooves or dents where the local anatomy is pushing or pulling with preferential forces on the electrode during the assimilation process. The assimilated electrode has thus undergone two phases of being molded to surrounding tissue: first, there is mechanical molding during injection and, second, a longer term molding to the local anatomy including in-growth of vessels and cells, and adhesion by a light fibrotic encapsulation.

The long term chronic mechanical characteristics of the assimilated structure are dependent on the wire diameter, compaction ratio, presence or absence of pre-loading with additives such as an immunoreactive agent, an anti-inflammatory agent, a hemostatic agent, and/or a pharmacological agent and surface modifications of the wires chosen as well as the presence or absence of non-conductive surgical threads used in the ex-vivo manufacturing process such as nylon or surgical silk.

Thinner wires (i.e. 25 micron) result in smaller spring tension of the structure, thereby minimizing the mechanical forces the naive tissue experiences in the encapsulation phase post implantation, leading to smaller encapsulation thicknesses. The smallest encapsulation separating the roughened and porous surface of the wire structure from the naive tissue were observed to be less than 50 microns, in certain cases as thin as approximately 20 microns, the equivalent of single digit cell layers.

Lower compaction ratios result in smaller spring tension of the structure, thereby minimizing the mechanical forces the naive tissue experiences in the encapsulation phase post implantation, leading to smaller encapsulation thicknesses.

The presence of nylon and especially the presence of surgical silk may cause a thicker encapsulation which is advantageous at the location where the wire structure electrode functions primarily as a lead, i.e., transporting electrical current from the skin to a nerve. Larger wires (at least 100 micron or 200 micron) which provide more mechanical strength against wire breakage during chronic interfacing or during the removal process, resulted in thicker encapsulation. There are instances where thicker encapsulation is advantageous, such as to avoid unintentional stimulation of surrounding tissues that are not the target tissue.

The ex-vivo manufacturing of the wire structures does not preclude them from being formed in-vivo into their final shape, such as by folding, meandering, spiraling, and thereby occupying a larger volume than the diameter of the delivery device, but only a slightly smaller volume than the cavity created in the body right before the deployment step. The ex-vivo manufacturing may include the filling of the voids (pores) inside the wire structure with a surgical glue or sealant, and waiting for it to cure prior to the placement into the body. Such a pre-cured filler does not have the function of physically gluing the wire structure into the bodily tissue, but instead may aid solely with modifying the assimilation response by the body and tissue ingrowth during the formation of the encapsulation.

Injectable wire structure electrodes made of pure 99.99% gold wire have been placed successfully subcutaneously in over 80 rodents (160+ devices), for varying implantation durations up to 180 days. No serious adverse events have occurred. As such, a strong safety profile for the device, sterilization method, injection location, and biological response has been demonstrated. Percutaneous conductivity measurements were conducted in these animals throughout the course of the device placement period.

In a subset of the devices, removal of the device was completed with the encapsulation layer left intact—intended for histopathological analysis to assess the biological response to the device. Histopathology covering 4 weeks to 180 days of implantation revealed the following conclusions. There was normal fibrous capsule formation, with the most prominent finding being the expected, stable and low inflammatory response to implanted material. Fibrotic response was variable—some devices had a higher degree of inflammatory and foreign body giant cells than others. Responses range from +1 to +3 (mild to moderate) responses, likely due to different handling of materials or inter-subject variability. There was no evidence of adverse granuloma, necrosis (e.g., no acute toxicity), tumor formation or infection.

Besides gold, additional materials are used in other embodiments to manufacture wire structure electrodes with varying mechanical and biological response properties and other facts including, without limitation, by patient allergy, target anatomy, physician preference, and material availability, as discussed elsewhere herein.

Embodiments with a combination of different wire thicknesses (25 micron and 100 micron) were tested and showed thicker outer encapsulation of the overall structure than pure 25 micron wire structures implanted for similar durations, which may be attributed to larger mechanical rigidity and resulting stiffness of the overall wire structures with larger diameter wires present. The achieved increase in mechanical strength with the addition of thicker diameter wires has advantages for the portion where the wire structure electrode functions more akin to a lead transporting electrical current or other energy rather than injecting the energy into the surrounding electrolyte.

Figure 4:
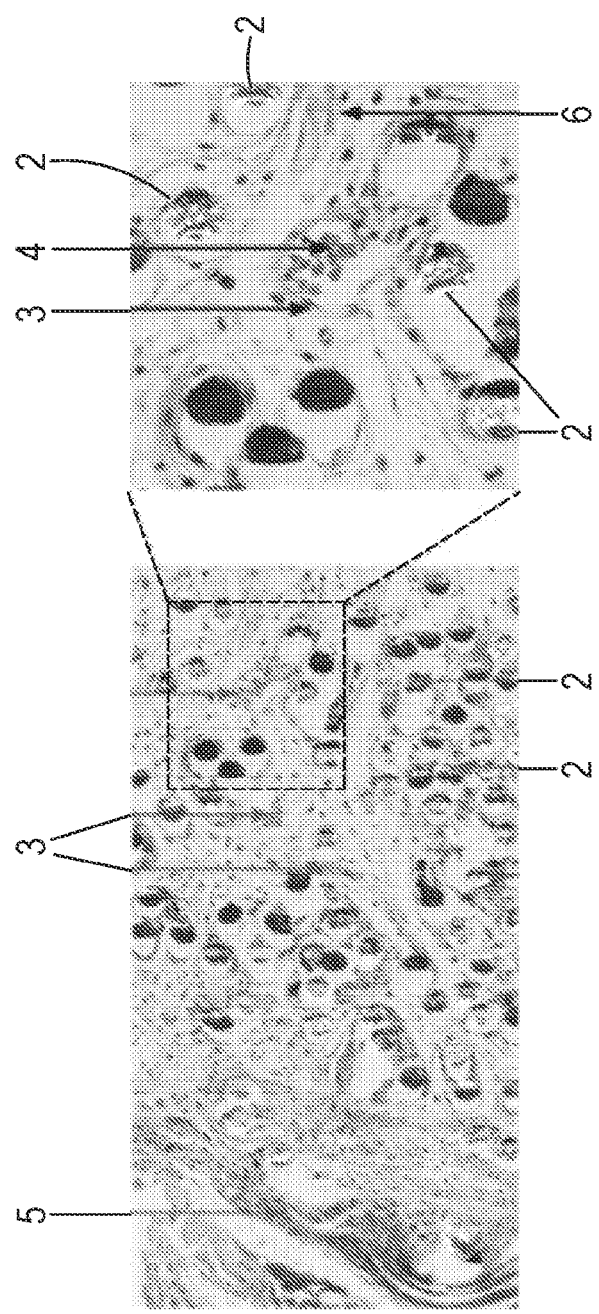
FIGS. 4 (a) & 4 (b) are two views of a histological section stained with trichrome to identify fibrous capsule and wire encapsulation with evidence of angiogenesis. This figure shows a folded wire structure comprising 25 micron gold wire at a low compaction density explanted after 60 days.

Further evidence of biocompatibility and assimilation includes FIGS. 4 (a)-(b) which are representative histological images of a cross-section of an explanted wire structure electrode (Trichrome Stained) identifying blood vessels 3 with red blood cells 4, the fibrous capsule 5 and collagen 6. The gold wires 2 of the wire structure are also indicated, with an enlargement showing the individual red blood cells within the vascular lumen, along with collagen fibers-indicative of assimilation and a normal fibrotic response. FIG. 4 (a) is an image of a histological section stained with trichrome to identify fibrous capsule and wire encapsulation with evidence of angiogenesis, and FIG. 4 (b) is an enlargement of a portion of FIG. 4 (a). These figures show 25 micron wire at a low compaction density implanted for 60 days.

Figure 5:
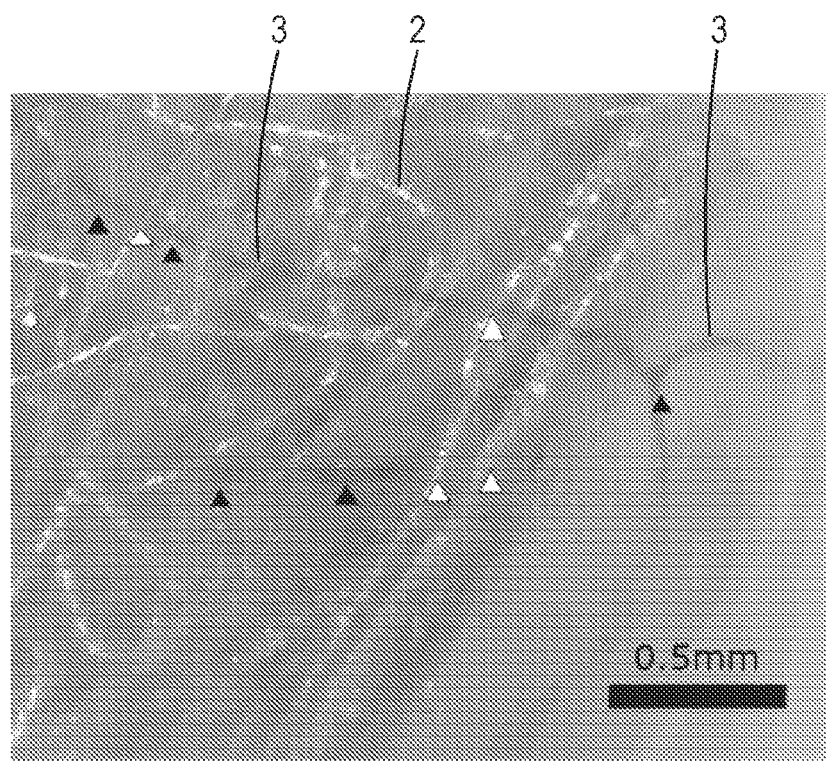
FIG. 5 is a photograph of blood vessels passing outside (black triangles) and through (white triangles) a folded wire structure after 8 weeks of implantation subcutaneously in a rodent preclinical model.

Further evidence of blood vessel formation is provided in FIG. 5, showing that vessels 3 pass underneath the wires 2 as suggested by the histological images discussed above. FIG. 5 is a photograph of blood vessels 3 passing over (black triangles) and through (white triangles) the wire structure electrode after 8 weeks of implantation subcutaneously in a rodent preclinical model.

Figure 6:
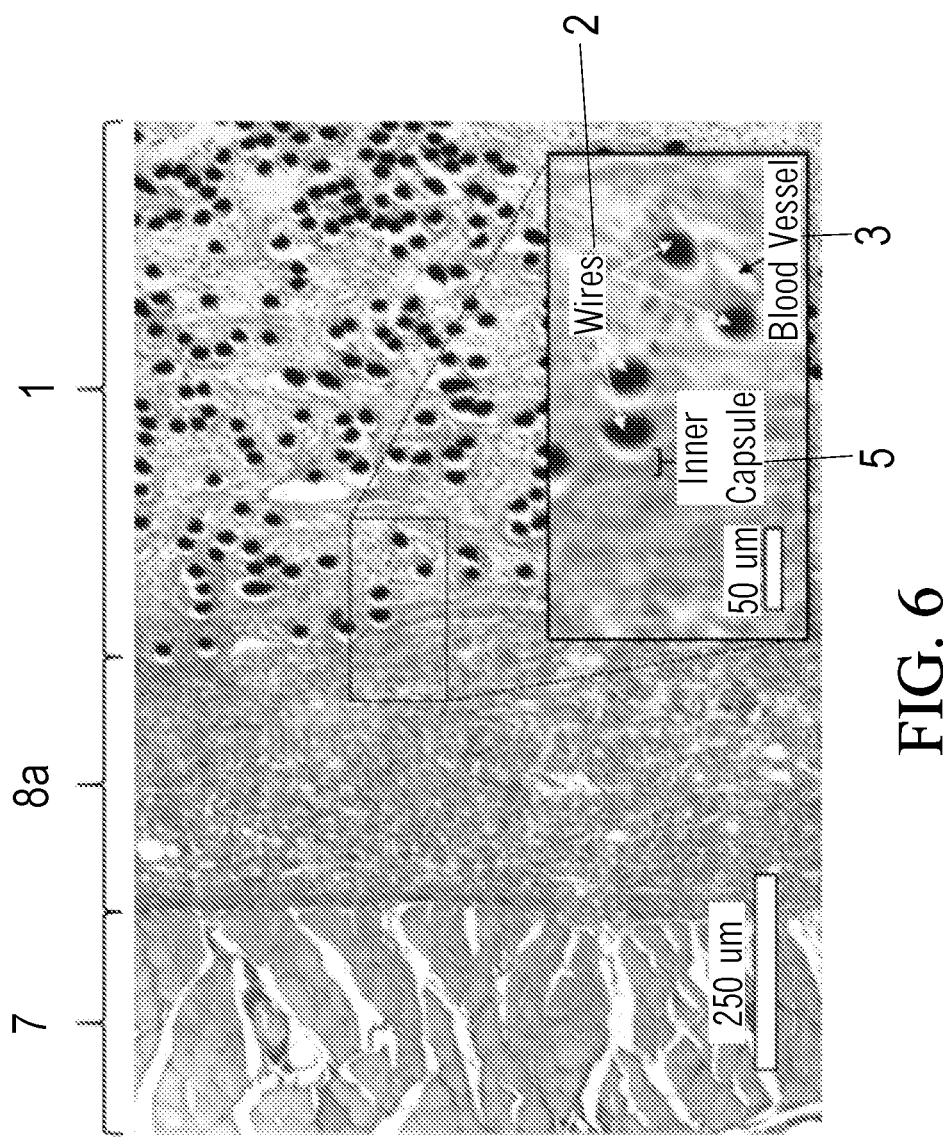
FIG. 6 is an image (and enlarged inset) of a cross section of the roughened and porous surface of a wire structure implanted subcutaneously and then explanted. The inner fibrotic capsule is less than 50 microns. Wires and blood vessels are shown in close proximity within the rolled wire structure.

FIG. 6 is an image (with enlarged inset) of a cross section of the roughened and porous surface of a folded wire structure implanted subcutaneously for eight weeks and then explanted. The inner fibrotic capsule 5 is less than 50 microns. Wires 2 and blood vessels 3 are shown in close proximity within the folded wire structure.

Figure 7:
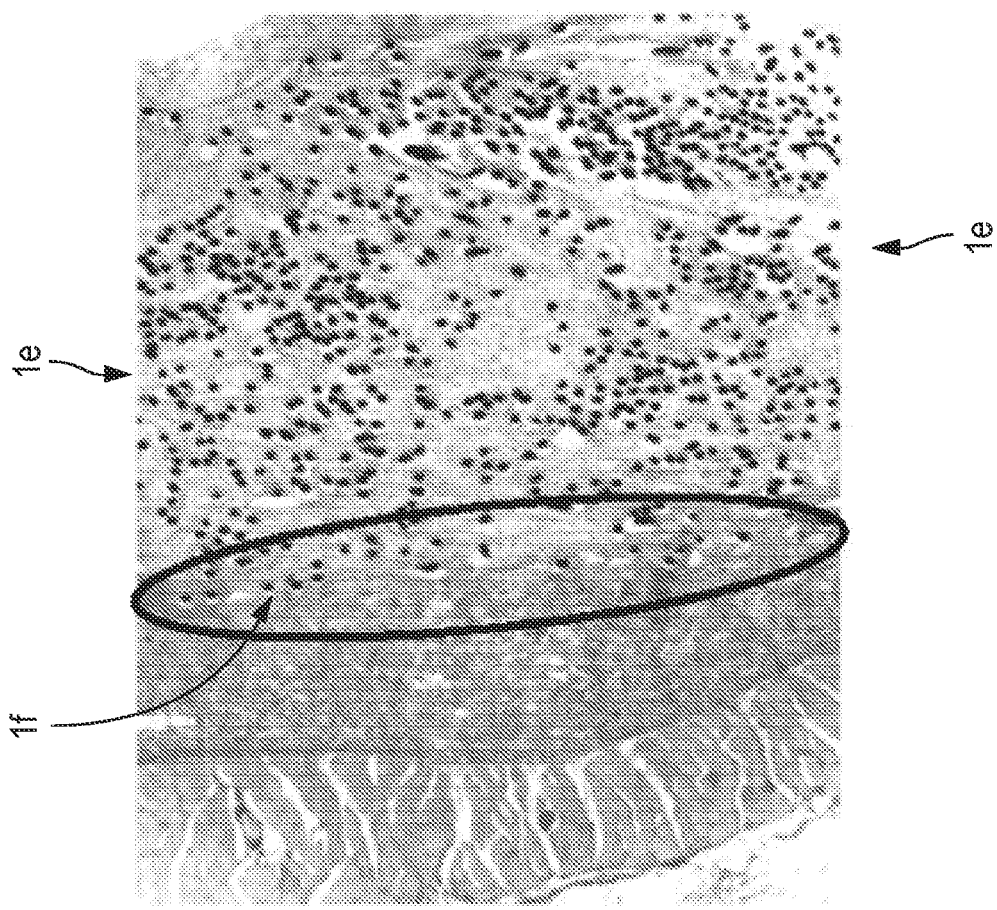
FIG. 7 is an image of a cross-section of an explanted wire structure electrode and surrounding tissue stained with trichrome.

FIG. 7 is an image of a cross-section of an explanted wire structure electrode 1 and surrounding tissue stained with Trichrome. An oval is drawn around the roughened and porous surface if which shows substantial in-growth and attachment of bodily tissues, demonstrating how the wire structure electrode described herein can become an assimilated electrode 1e, that is, integrated with the surrounding tissue.

c. Flexible, Bendable, Stretchable, Deformable

Figure 8C:
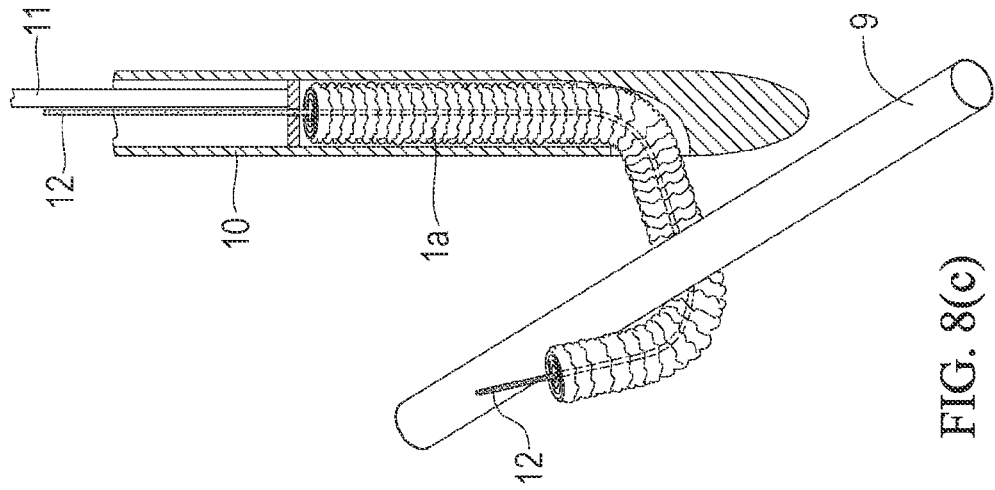
FIG. 8 (a) is a section view of a schematic showing a method of placement of a wire structure (here, rolled) being pushed from a cannula with a plunger.
Figure 8B:
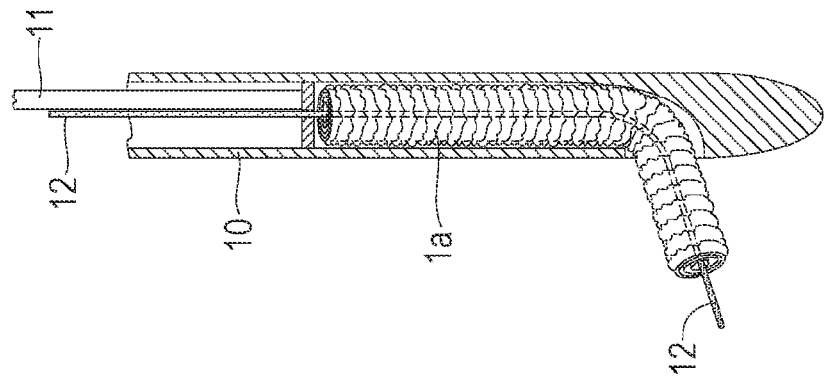
Figure 8A:
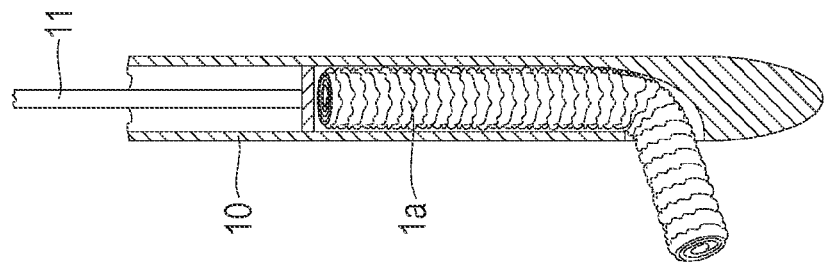

FIG. 8 (a) is a section view of a schematic showing a method of injection of a rolled wire structure 1a being pushed from a cannula 10 with a plunger 11. FIG. 8 (b) is similar, except the rolled wire structure here has an embedded guide wire 12 and the plunger comprises an opening for the guidewire. FIG. 8 (c) shows the rolled wire structure with a guide wire 12 in a "J" shape 1a1 at the tissue target 9. As depicted, the "J" shape is placed around a nerve, with the purpose of providing greater circumferential coverage of the nerve to induce more effective depolarization.

Figure 9A:
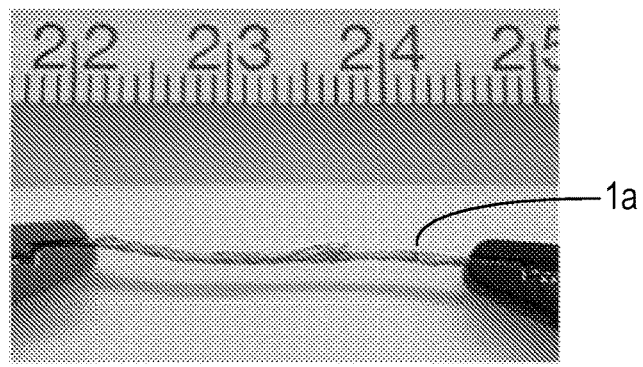
FIG. 9 (a)-(c) depict strain versus conductivity: (a) is pre-strain at 25 mm in length, (b) is post-strain at 77 mm, and (c) is a graph depicting strain versus conductivity.
Figure 9B:
Figure 9C:
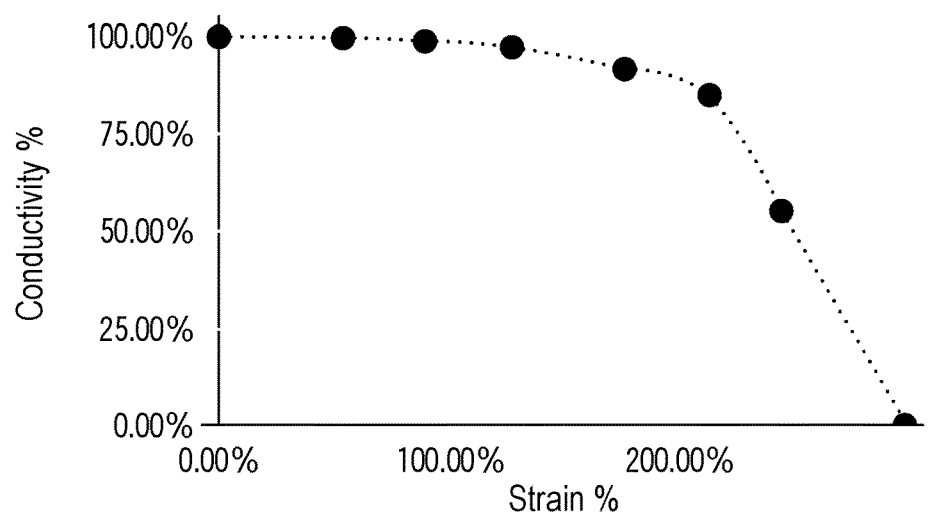

FIG. 9 (a)-(c) depict strain versus conductivity in a rolled wire structure 1a: FIG. 9(a) shows the structure in pre-strain at 25 mm in length, FIG. 9(b) shows the structure post-strain at 77 mm, and (c) is a graph depicting strain versus conductivity. Strain was calculated as (length.pre-length.post)/length.pre, where 100% strain equates to a doubling in length. Conductivity was measured with a certified LCR unit measuring impedance at 1 kHz.

d. Rolled Wire Structures

One method of producing a rolled wire structure includes providing at least one highly conductive wire as described herein, and wrapping it around at least one mandrel 13 to form spools 14 of overlapping strands of wire. In one embodiment, the at least one highly conductive wire 2 includes two or more wires twisted or braided to form rope, or two or more twisted or braided ropes 1c. The wire may be fed from one or multiple sources and materials to adjust product properties within desired parameters.

Figure 10:
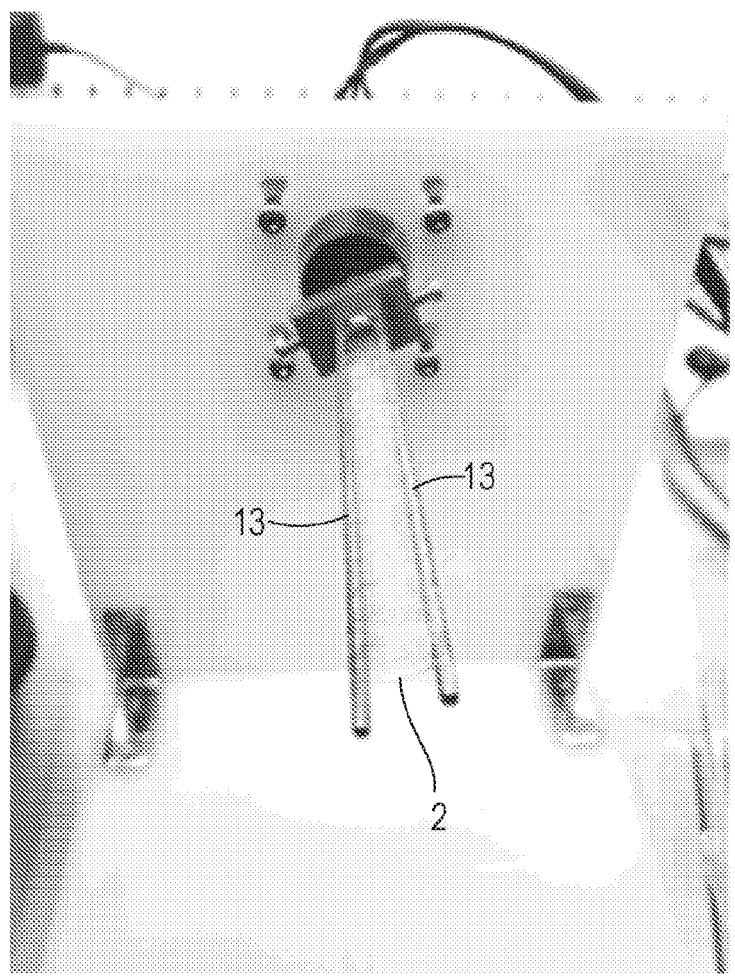
FIG. 10 is a photo of wire wrapped around a plurality of mandrels.
Figure 11A:
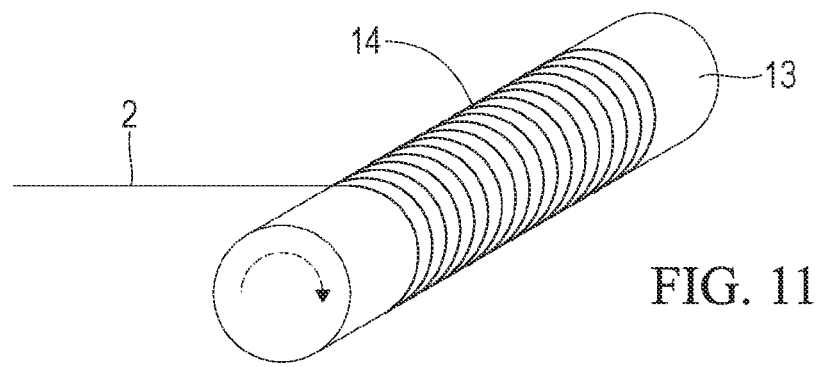
FIG. 11 (a)-(d) are schematics showing steps for making a rolled wire structure without a guidewire in the center.
Figure 11B:
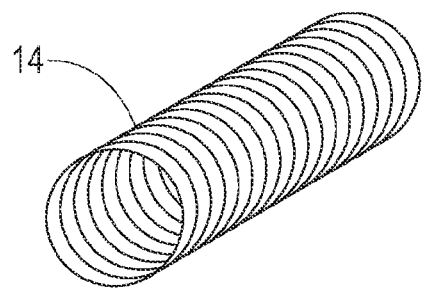
Figure 11C:
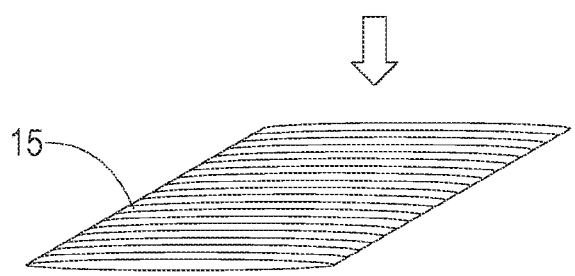
Figure 11D:
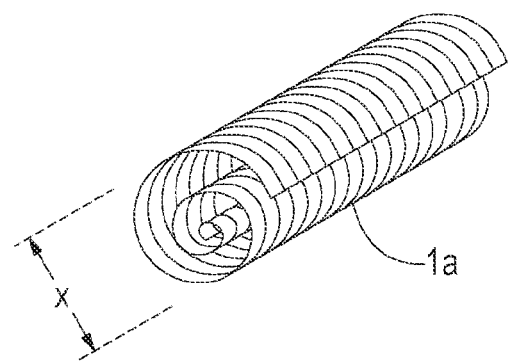
Figure 12A:
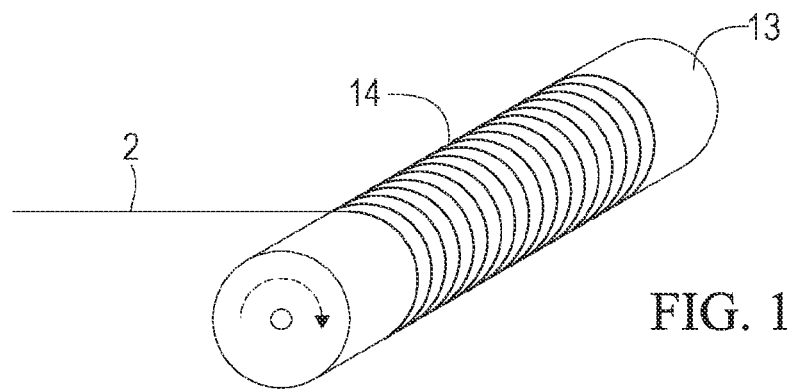
FIGS. 12 (a)-(d) are schematic drawings showing steps for making a rolled wire structure with a guidewire in the center.
Figure 12B:
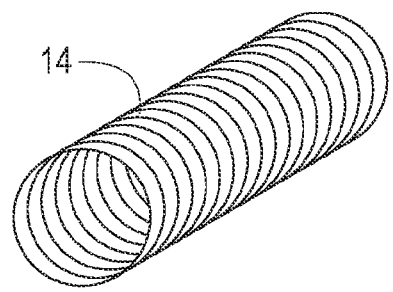
Figure 12C:
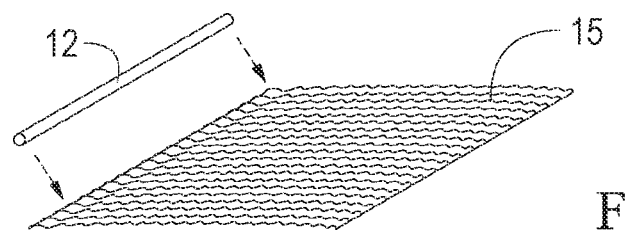
Figure 12D:
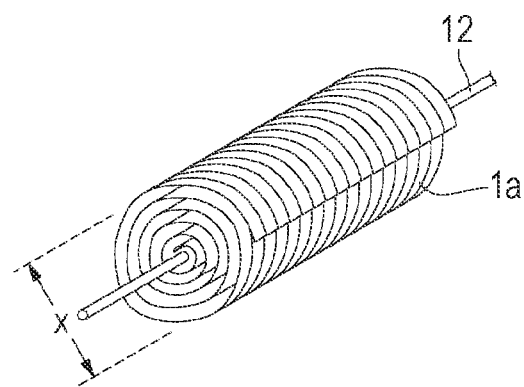

Additionally, in other embodiments, the wire 2 is wrapped around multiple mandrels 13. FIG. 10 is a photo of gold wire wrapped around a plurality of mandrels 13 for ease of removal, the ability to create additional variations, or control of the initial geometry prior to injection.

Additional steps in manufacturing methods include "flattening" the spools into a flattened spools 15, in one embodiment, which has innumerable overlapping loops and folds. Then the flattened spools 15 are rolled to produce the rolled wire structures which are shown in the figures herein. The number of rolls varies depending on the length of the spools and the number of windings around the mandrel. In one embodiment the rolled wire structure starts with spools made from 15 meters of 25 micron wire, which is flattened into a sheet approximately 8 cm×1.5 cm. The sheet is then rolled between two parallel surfaces with controlled and variable spacing for cumulative distance (bi-directional) of at least 3× the width, shortest dimension, of the sheet to produce a rolled wire structure whose dimensions are approximately 8 cm in length and 1 mm in diameter.

Figure 13A:
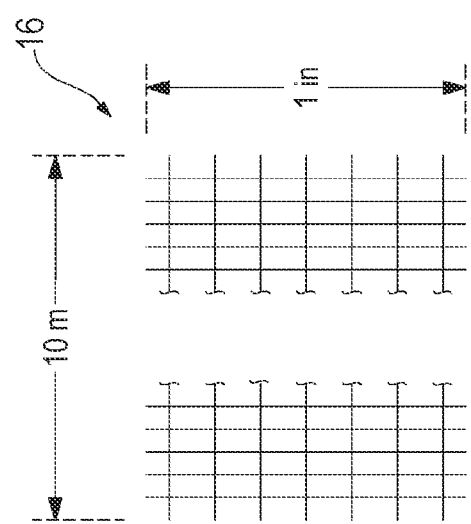
FIG. 13 (a) is a schematic of a woven wire mesh as a starting point for manufacturing a rolled wire structure, (b) shows a rolled wire structure from the wire mesh, and (c) shows a rolled wire structure from the wire mesh containing a guidewire in the center.
Figure 13B:
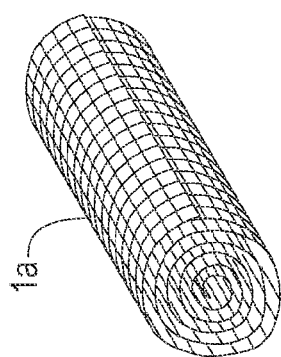
Figure 13C:
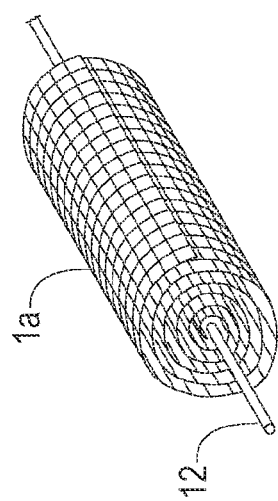

FIGS. 11 (*a*)-(*d*) show schematics of steps for a method of manufacturing one embodiment of a rolled wire structure without a guidewire in the center. Wire 2 is fed to a mandrel 13 and spools 14 wrapped around the mandrel are shown in FIG. 11(*a*), the spools removed from the mandrel are in FIG. 11(*b*), the flattened spools 15 prior to rolling are shown in FIG. 11(*c*), and the rolled wire structure is shown in FIG. 11(*d*). FIGS. 12 (*a*)-(*d*) are schematics showing steps for a method of manufacturing a rolled wire structure with a guide wire 12 in the center. The wire 2 is fed to a mandrel 13 and spools 14 wrapped around the mandrel are in FIG. 12(*a*), the spools removed from the mandrel are shown in FIG. 12(*b*), the flattened spools prior to rolling with a guidewire are shown in FIG. 12(*c*), and the rolled wire structure with the guidewire in the center is shown in FIG. 12(*d*). FIG. 13 (*a*) is a schematic of a woven wire mesh 16, 10 meters in one embodiment, as a starting point for manufacturing a rolled wire structure, FIG. 13(*b*) shows a rolled wire structure 1*a* resulting from rolling the woven wire mesh 16, and FIG. 13(*c*) shows the rolled wire structure from the woven wire mesh 16 containing a guide wire 12 in the center.

Figure 14:
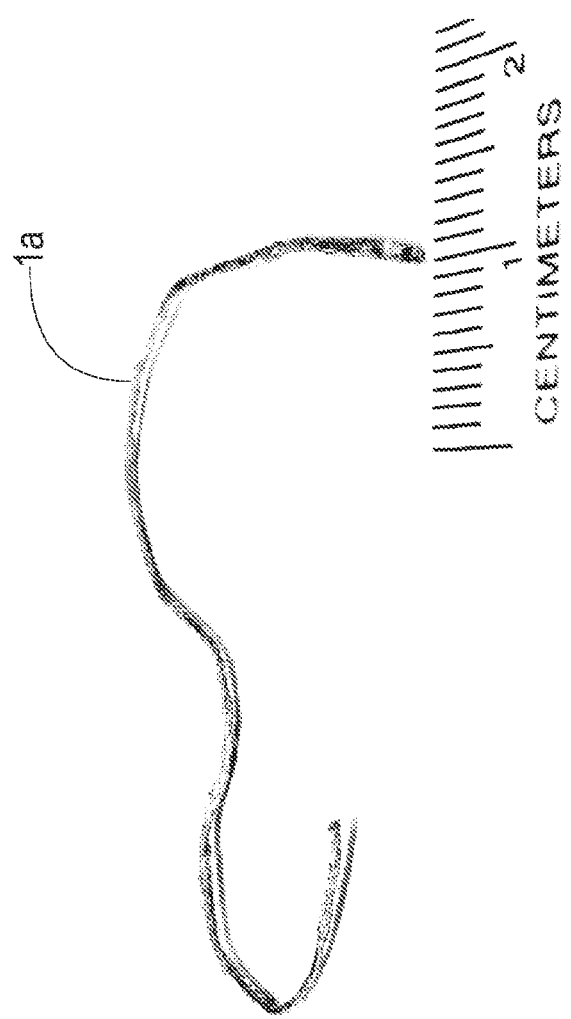
FIG. 14 is a photograph of a rolled wire structure comprising gold wire seen with a millimeter scale.

FIG. 14 is a photograph of a rolled wire structure 1*a* comprising gold wire seen with a millimeter scale which was manufactured in accordance with the steps shown in FIG. 11 and FIG. 13.

FIG. 15 (*a*)-(*d*) are images showing an implanted J-shape 1*a*1 wire structure electrode. Left hand and right hand images of FIG. 15(*a*) are external photographs of a J-shape 1*a*1 rolled wire structure of 1 mm diameter, 3 cm length implanted subcutaneously for 18 days in the subcutaneous region of a rodent. The three cross section images FIGS. 15(*b*)-(*d*) are from the same animal under ultrasound visualization showing epidermis 8*b*, dermis 8*c*, subcutaneous layer 8*a* and muscle 7. The oval region in left hand image FIG. 15(*a*) shows the J-shape 1*a*1 corresponds respectively to image FIG. 15(*b*) which is normal skin 8, image FIG. 15(*c*) which is the long shaft 1*a*1*a* of the J-shape, and image FIG. 15(*d*) taken near the bottom of the shaft 1*a*1*a* of the J and at the loop 1*a*1*b* of the J.

Figure 15A:
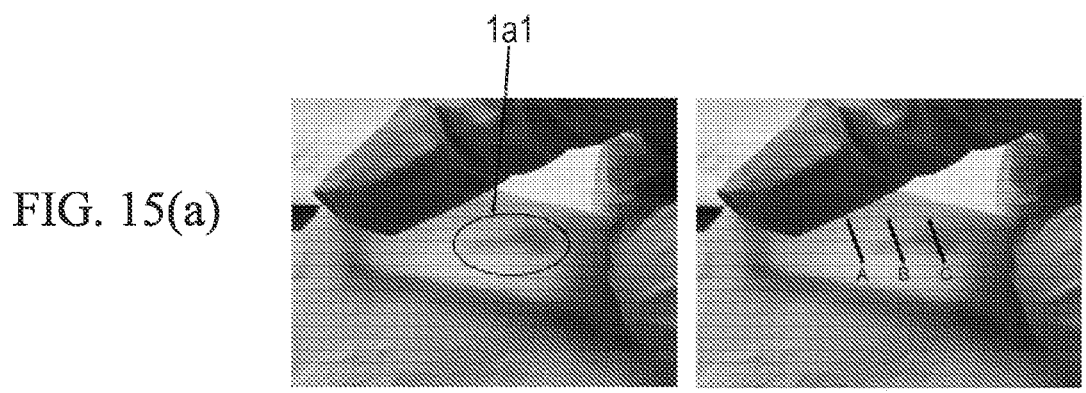
FIG. 15(a) shows two external photographs of a J-shaped rolled wire structure of 1 mm diameter, 3 cm length implanted subcutaneously for 18 days in the subcutaneous region of a rodent.
Figure 15B:
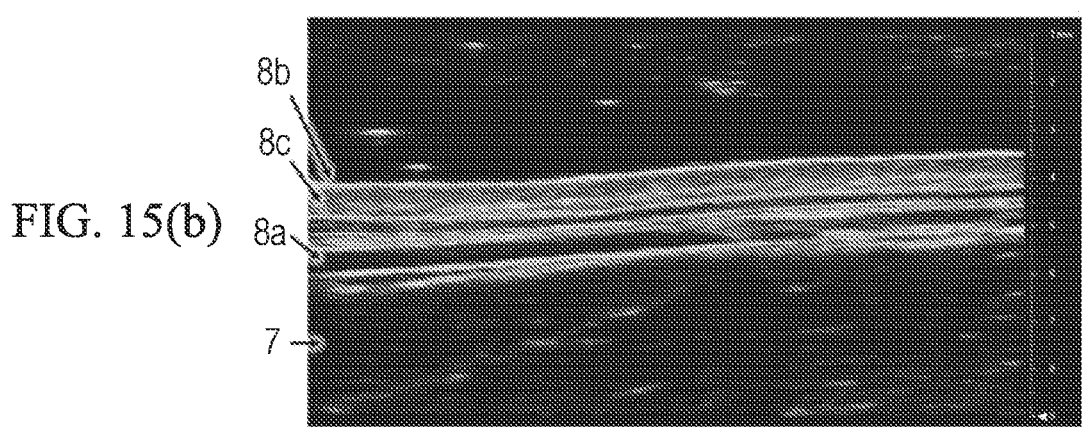
FIGS. 15(b)-15(d) are three cross section images from the same animal under ultrasound visualization. The oval region in the left hand image of FIG. 15(a) shows the J-shape, and the section lines A, B, C in the right hand image of FIG. 15(a) correspond respectively to image FIG. 15(b) which is normal skin, image FIG. 15(c) which is the long shaft of the J, and image FIG. 15(d) taken through the bottom of the shaft of the J and at the loop of the J.
Figure 15C:
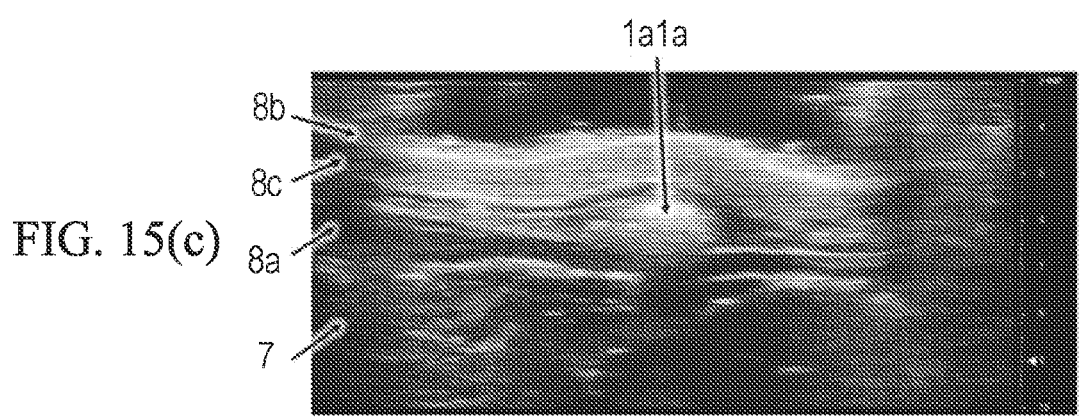
Figure 15D:
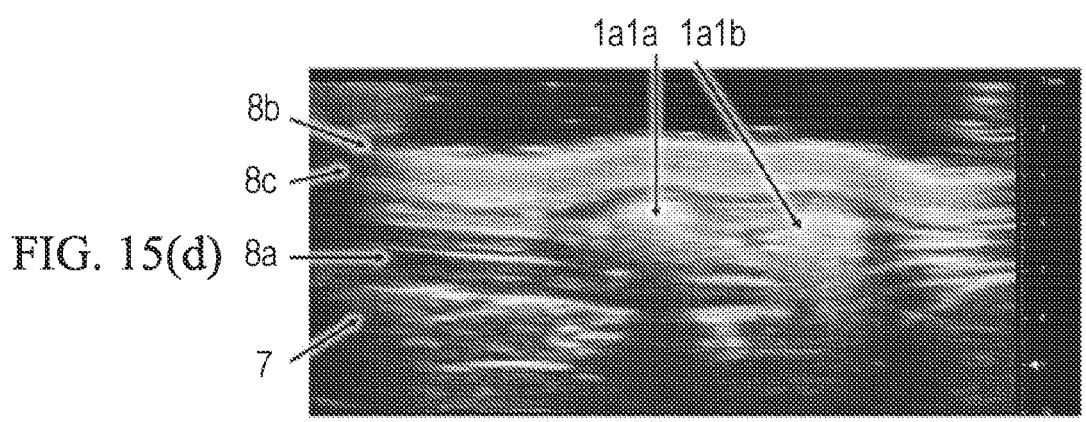
Figure 15A:
Figure 15A:
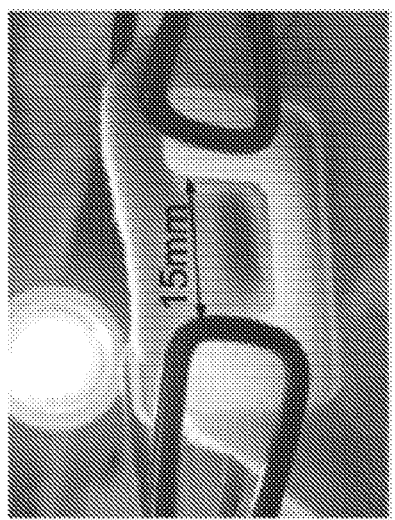
Figure 15A:
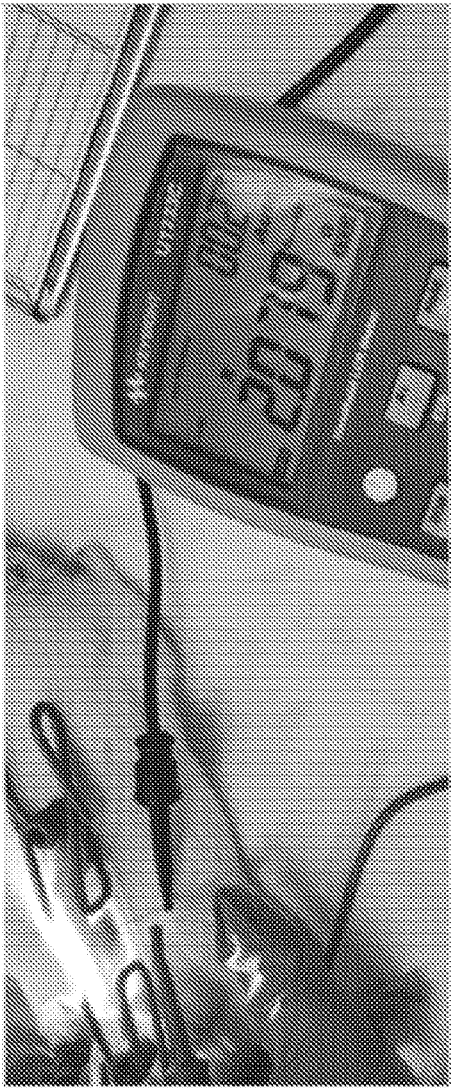
Figure 17A:
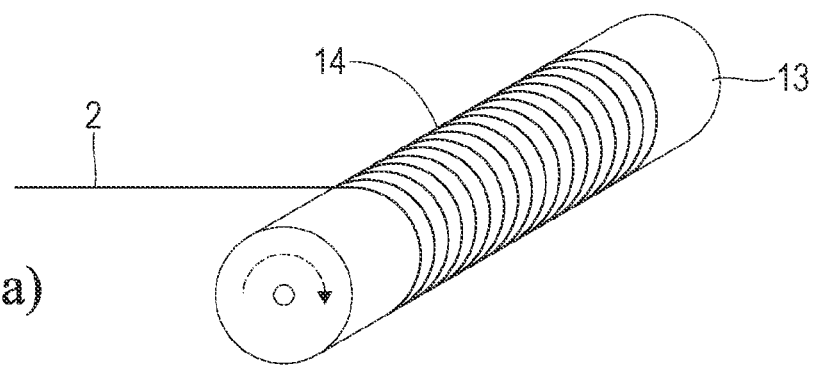
FIGS. 17 (a)-(d) are schematics showing steps for a method of making a folded wire structure. The wire feeds to a guidewire which serves as mandrel and spools wrapped around the mandrel are shown in FIG. 17(a), and the folded wire structure is shown in FIG. 17(d).
Figure 17B:
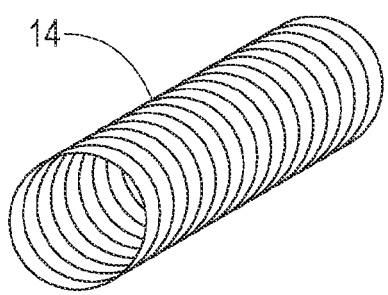
Figure 17C:
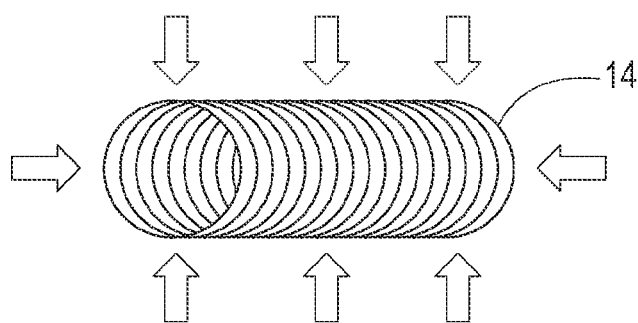
Figure 17D:
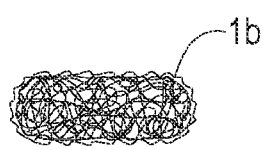

FIG. 15A (a)-(c) show an impedance test on a wire structure electrode having been implanted for four weeks and measuring 2.079 ohms.

In one embodiment the rolled wire structure can then be compacted resulting in even more numerous overlapping loops and folds with a continuous pathway for energy transmission. These wire structures may then be created by compacting the spools 14 into a mold 17 of predetermined shape with minimal pressure. FIGS. 16 (*a*) & (*b*) depict an embodiment of a mold for compacting any wire structure electrode. That is, if desired, the rolled wire structure in FIG. 11 (*d*) or FIG. 12 (*d*) may be compacted even further. FIGS. 16 (*a*) and 16(*b*) are a respectively a side view and a perspective view of one embodiment of a mold for compacting a rolled wire structure. The compaction in a mold, as in FIGS. 16 (*a*)-(*b*), results in a further compacted rolled wire structure (or any other wire structure electrode), which may then be loaded into a cannula 10 (or other tubing) of predetermined dimensions. Compaction from both ends to a final length provides a wire structure electrode as illustrated herein. Although there are many different combinations of dimensions for different embodiments, an illustrative list of dimensions for the injectable wire structure electrode includes 1×1×10 mm, 2×2×10 mm, 1×2×10 mm, 1×1×30 mm, and 0.5×1×50 mm.

e. Folded Wire Structures

In one embodiment, the initial step is wrapping at least one highly conductive wire around at least one mandrel 13 to create spools 14 which can then be compacted resulting in numerous overlapping loops and folds with a continuous pathway for energy transmission. These wire structures may then be created by compacting the spools 14 into a mold 17 of predetermined shape (e.g., 1.5×4×10 mm) with minimal pressure. The compaction in a mold results in a folded wire structure. Compaction from both ends in a mold to a final length in a way similar to FIG. 16 (*a*)-(*b*) provides an injectable wire electrode as illustrated herein. FIGS. 16 (*a*)-(*b*) depict an embodiment of a die for compacting a folded wire structure. The folded wire structure is next loaded into a cannula 10 (or other tubing) of predetermined dimensions.

FIGS. 17 (*a*)-(*d*) are schematics of steps for a method of making one embodiment of a folded wire structure. The at least one wire 2 feeds to at least one mandrel 13 and spools 14 wrapped around the mandrel are shown in FIG. 17(*a*), the spools 14 removed from the mandrel are in FIG. 17(*b*), the compaction of flattened spools 15 with force applied in the direction of the arrows is shown in FIG. 17(*c*), and the folded wire structure is shown in FIG. 17(*d*).

f. Wrapped Wire Structure Electrodes

Figure 18A:
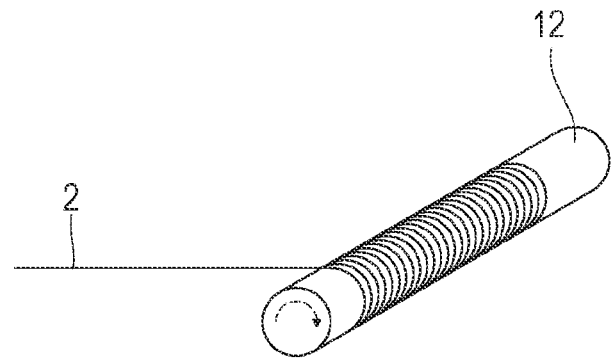
FIGS. 18 (a) and (b) are schematics showing steps for a method of making a wrapped wire structure. The wire feeds to a guidewire which serves as mandrel and spools wrapped around the mandrel are shown in FIG. 18(a), and the wrapped wire structure is shown in FIG. 18(b) including an inset for greater detail, and in a photo, FIG. 18 (c).
Figure 18B:
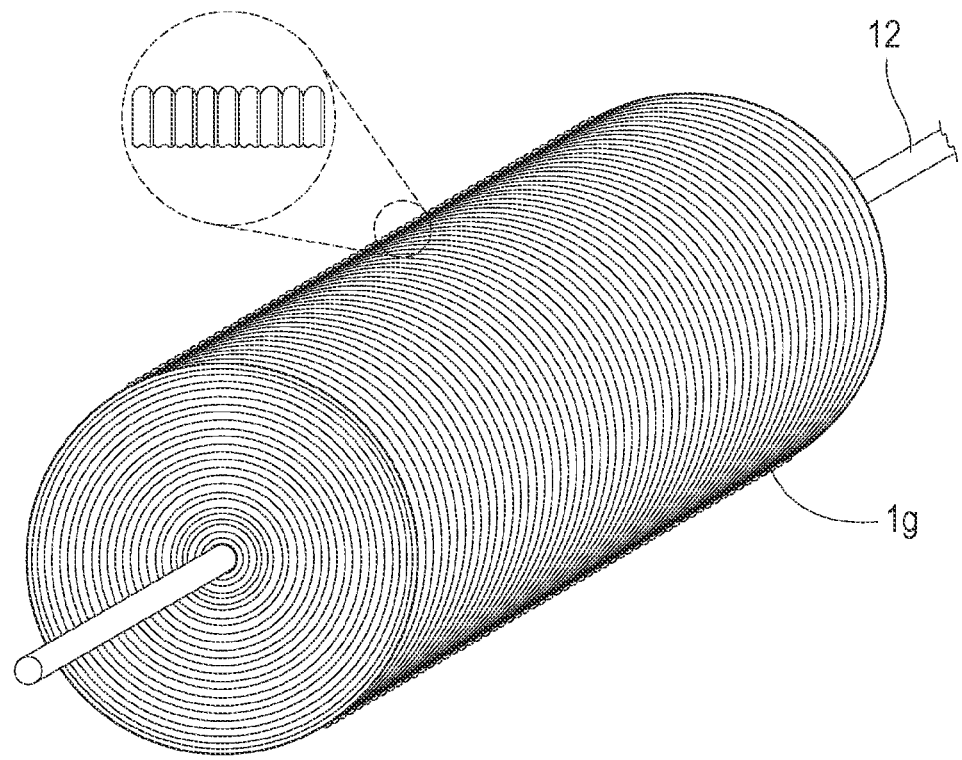
Figure 18C:
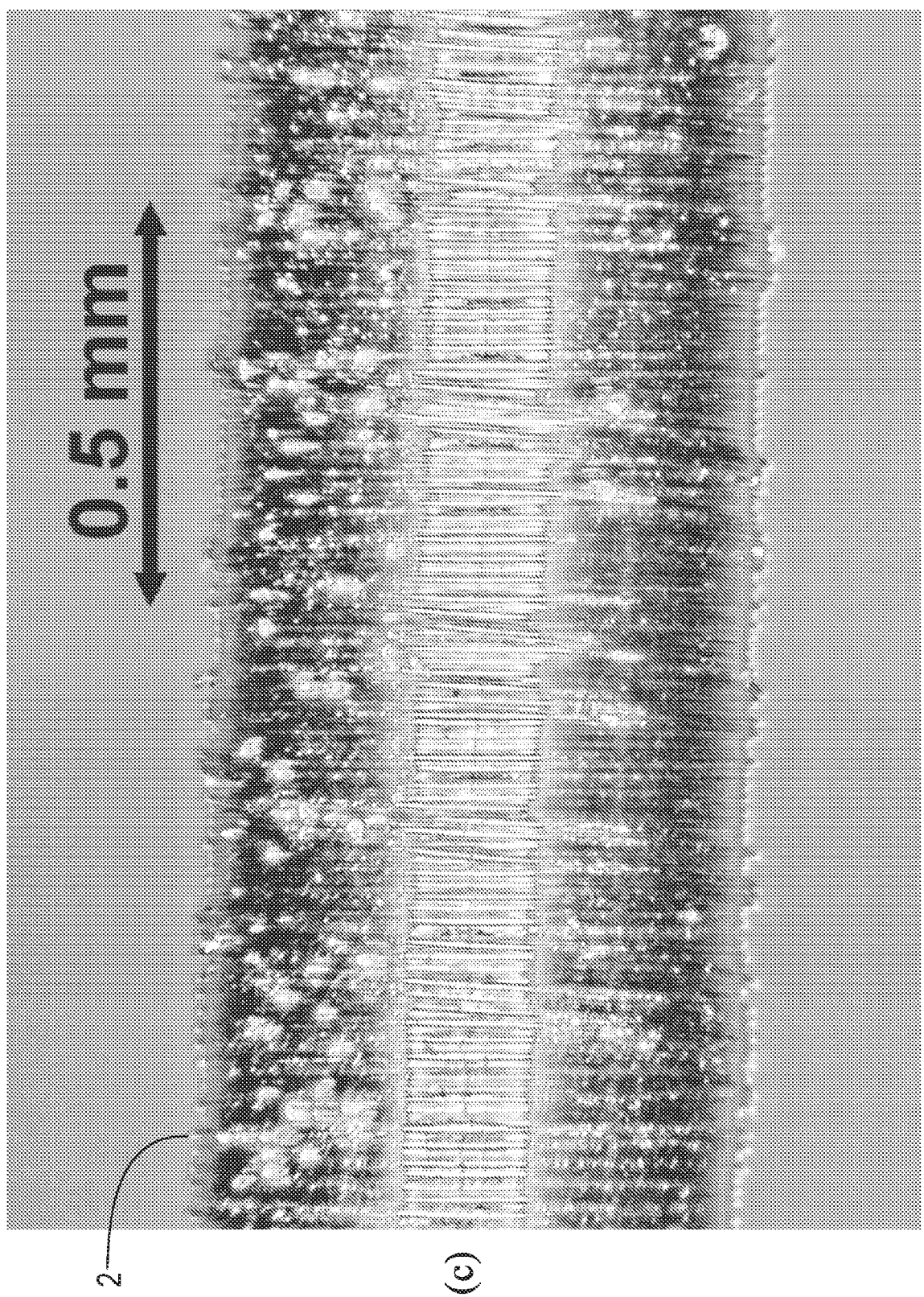
Figure 19A:
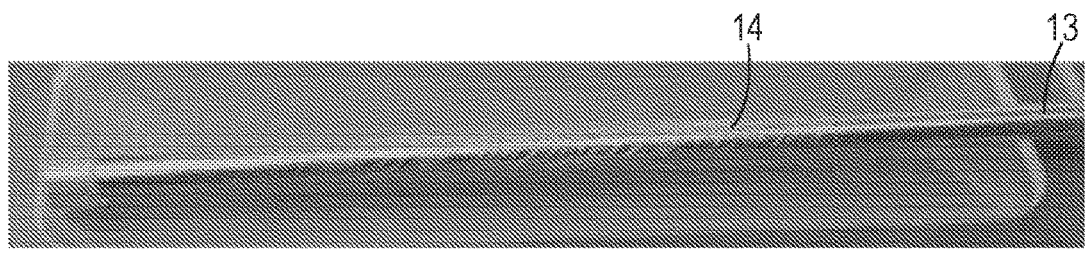
FIG. 19(a) shows wire wrapped in spools around a mandrel.
Figure 19B:
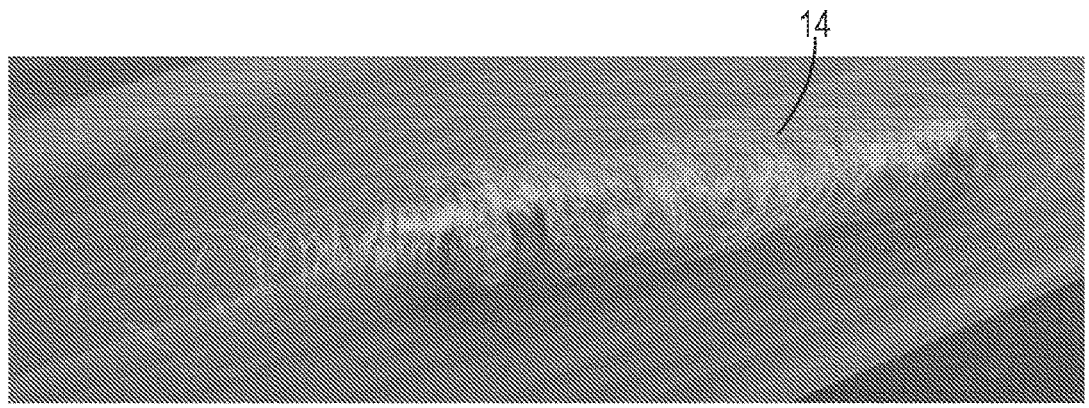
FIG. 19(b) shows the spools removed from the mandrel, and FIGS. 19 (c) and (d) show compaction of the spools.
Figure 19C:
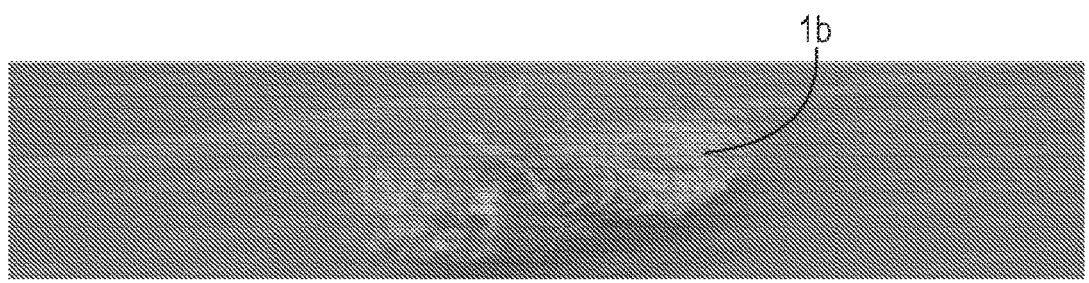
FIGS. 19 (a) (d) are photographs of steps in a method of manufacturing gold wire structures from 25 micron gold wire to form spools which can then be used to make a rolled or folded wire structure.
Figure 19D:
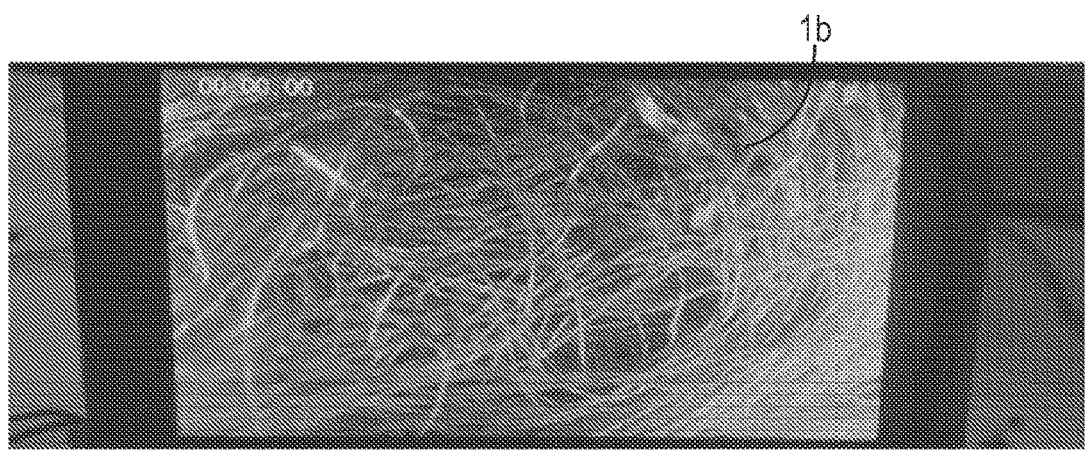
Figure 19A:
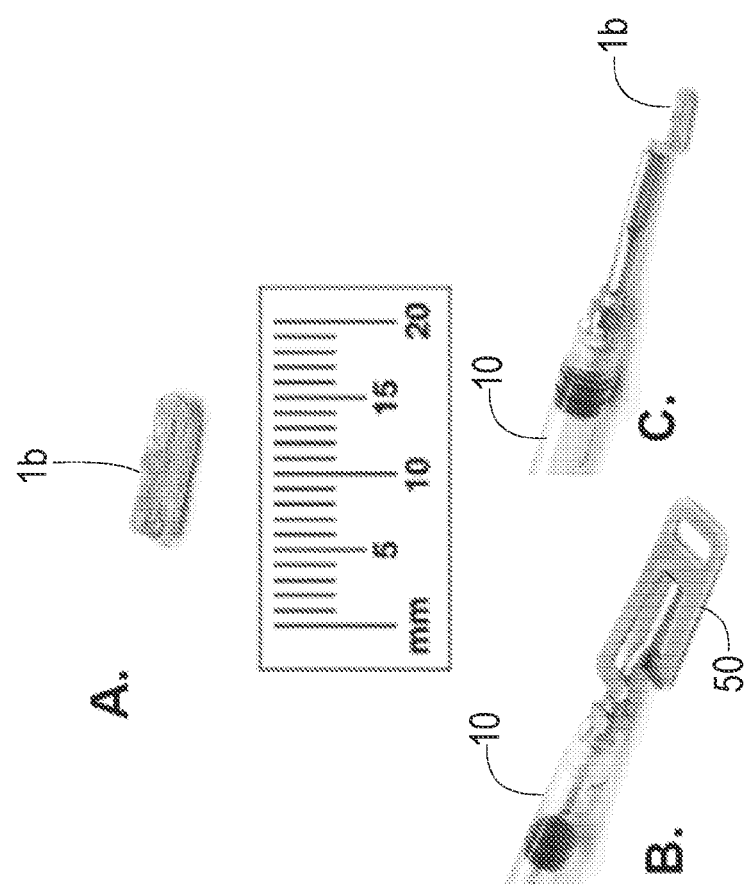

FIG. 18 (*a*)-(*b*) show a schematic embodiment of a wrapped wire structure electrode 1*g* which is made by wrapping wire 2 around a thin guide wire 12 which will be injected with the wire electrode, instead of wrapping around a reusable mandrel. The wrapped structure 1*g* may be wrapped many more times around the guide wire 12 than the rolled or folded wire structures are wrapped around mandrels. This method also produces the roughened and porous surface if because the wires, without reinforcers discussed below, are not bound together and move in relation to each other in response to force. FIG. 18 (*c*) is a photo showing an enlarged portion of an embodiment of a 25 micron diameter gold wire wrapped around a 0.030 inch diameter needle, that is, a size suitable for a guide wire.

FIGS. 19 (*a*)-(*d*) are photographs of 25 micron diameter gold wire FIG. 19(*a*) spools 14 wrapped around a mandrel 13, FIG. 19(*b*) spools 14 removed from the mandrel FIG. 19(*c*) compacted gold wire spools prior to implantation and FIG. 19(*d*) a close up of a portion of the spools in FIG. 19(*c*). Photographs of folded wire structures ready for implantation are found in FIG. 19A, along with a universal fixture allowing it to be affixed any syringe.

g. Twisted or Braided Wire Structures

Twisting or braiding wires can be achieved by positioning both ends of wires of similar length between two fixtures which can rotate to achieve the desired density. The number of strands are limited to machine complexity, but upwards of a 100 strands may be incorporated into a twisted or braided structure.

FIGS. 20 (*a*)-(*c*) are three images of twisted or braided strands of gold wire, with the number of strands left to right being 1, 6, 10, 20 and 40: FIG. 20(*a*) closest, FIG. 20(*b*) next closest, and FIG. 20(*c*) farthest views. Depending on the number of twists in a given length, the twisted or braided structure 1*c* can be very tightly wound leaving very little space or voids, or the structure can be loosely wound and therefore have greater space within the bulk shape. In any event, the twisted or braided wire structure as shown in FIGS. 20 (*a*)-(*c*) also has a roughened and porous surface if in that there are numerous ridges between each of the wires and wound embodiments also are porous when subjected to force because they are not bound together tightly.

h. Other Techniques

There are numerous other ways to form an injectable wire structure electrode as long as sufficient density can be achieved for conductivity. FIG. 21 (a) depicts patterns of wrapping wire around a scaffold 18, here rectangular, which may comprise dissolvable material or a thermoplastic to be heated to allow the wrapped wire to collapse and be removed; and FIG. 21 (b) depicts wrapping at least two wires of different diameter around a single mandrel 13, each wire 2 out of phase with the other.

i. Thermal Energy

In addition to use in electrical stimulation, the wire structure electrode can be used to transfer thermal energy within the body. Similar to the placement approaches used to transfer electrical energy, the wire structure may be placed near, through, into, or around a target structure within the body that is sufficiently deep within the body that a thermal modification of said structure cannot easily be achieved from the body's surface directly when thermal energy is just applied to the skin of the body. Thermal energy is dissipated within the body, the gradient of thermal energy dropping off rapidly as the living body attempts to retain a thermal balance on the inside and heat or cold applied to the outside of the body does not easily penetrate to deeper locations, such as 1 to 2 cm deep inside the body.

In such a case, the wire structure may be utilized as a conductor of thermal energy. Said folded wire structure may be either transporting thermal energy from a location just beneath the surface of the body to a location deeper within the body (i.e. 2 cm measured perpendicular from the bodily surface), or it may be transporting thermal energy from a location deeper within the body (i.e. 2 cm deep) to a location just beneath the surface of the body. For the instance where the folded wire structure transports thermal energy from deeper within the body to a more shallow location near the surface, the effect is a cooling effect of the deeper location within the body, thereby affecting the metabolic activity of the tissues that are thermally close proximity to the end of the folded wire structure that is deeper within the body. This, for example, enables the application of cooling a nerve at a location so deep inside the body that it can't be cooled easily from the outside of the body to achieve a thermal nerve block effect deeper within the body by just cooling the skin of the body with underlying folded wire structure, effectively transferring the cold application from the skin to the layer deeper within the body. Heating or cooling applied to the surface of the skin is preferentially conducted along the folded wire structure to a location deeper within the body, thereby affecting the metabolic activity a target structure deeper within the body. By cooling a nerve deeper within the body, the nerve's ability to conduct neural signals may be lowered, effectively providing a nerve block to a nerve deep within the body. As nerves for entire body parts such as a foot, a knee, a wrist are transported by nerves (genicular nerve for knee, posterior tibial nerve or saphenous nerve for foot, ulnar, median and radial nerve for arm, hand and wrist, one may utilize the approach to block pain preferentially in said larger volume body part by blocking neural activity in a larger nerve which in general will be located deeper within the body and often so deep that a cooling from the skin may be impractical or impossible without the prior placement of a folded wire structure as described herein.

Thermal interfacing to said folded wire structure may be achieved by either placing a source or drain of heat on the surface of the body with underlying folded wire structure implanted in the subcutaneous tissue of the body and reaching to a deeper location within the body. In this case the thermal energy conducts through the skin into the subcutaneous tissue transcutaneously. Alternatively, a needle based approach may be used to achieve a direct thermal conduction pathway by having thin needles pierce the skin of the body and mechanically interface with the folded wire structure in the subcutaneous tissue of the body. In that case the thermal conduction is percutaneous as the primary path of thermal energy is along the needles (e.g. metallic needles) conduct the majority of the thermal energy between the outside of the body and the subcutaneous tissue location of the folded wire structure, from where the thermal energy is further conducted to or from into the deeper location within the body.

j. Compaction Ratio

The compaction ratio is the quotient of material volume to total volume of the final product after manufacturing. This ratio affects the biological response, via the void space for cellular ingrowth and angiogenesis. The ratio is therefore on one end (high) constrained by a desired biological response. On the low end, bulk conductivity (and therefore interfacing impedance) becomes the constraining factors. For the wire structure electrodes described herein, the compaction ratio may be empirically calculated from wire length, nominal diameter, and the final compaction volume as defined the manufacturing process.

Provided here are calculations for the following manufacturing inputs for the production of one embodiment of an injectable wire structure electrode using 25 micron gold wire which is 15 meters in total length to reach a final compaction size of 1.5×4×10 mm. In one embodiment, the selected manufacturing process ex vivo comprises the steps wrapping for form spools and then compacting the spools. With the above parameters set in place, compaction ratio calculations are thus:

Material Volume:(25 microns/2)^2×pi( )×15 meters= (0.025/2)^2*pi( )*15,000=7.36 mm^3

Total Compaction Volume:1.50*4.00*10.0=60.0 mm^3

Compaction Ratio:7.36/60.0=12.3%

Folded wire structures that are made, for example, from 25 micron gold wire and compaction ratios below 25% provide inter-wire spacing averaging above standard cell diameters (2-20 microns). This compaction ratio is dependent primarily on wire diameter used to manufacture the structure. A low enough compaction ratio provides adequate voids or spacing to allow for angiogenesis. Folded wire structures of gold wire provide adequate voids or spacing to allow for angiogenesis and fibrous capsule formation not only around the entire wire structure, but also around individual wire loops and folds within the entire structure. Folded wire structures of gold wire with compaction ratios above 25% and below 50% provide smaller voids and less spacing to allow for angiogenesis and fibrous capsule formation not only around the entire wire structure, but also around individual wire loops and folds within the entire structure. Folded wire structures of gold wire with compaction ratios above 50% and below 90% provide only very small voids and much less spacing to allow for lesser angiogenesis and fibrous capsule formation not only around the entire wire structure, but also around individual wire loops and folds within the entire structure. Bulk conductivity on the low end is driven by two dimensional density within a plane through the injectable wire electrode perpendicular to the axis of a percutaneous interfacing needle, as well as the diameter of that needle. These variables affect both pore size and potential for interfacing points. For example, should a 0.35 mm (30 gauge) needle be used, pores must should therefore be smaller than 0.35 mm across. Simply taking the ratio of wire diameter to needle size, we can get a rough estimate of the lower bound compaction ratio, of approximately 0.025/0.35=7.14%. To aid with the intrinsic tension the folded wire structure provides to any indwelling needles, the folds of the wires provide for a natural spring action that allows for a mechanically stable connection that stabilizes the electrical interface for percutaneous needles independent of the pore size theoretically achieved based on the folded structure's compaction ratio alone.

Compaction may be achieved, as mentioned, in an infinite variety of "mold" configurations. In order to form rope-like gold wire injectable wire electrodes for volumetric injection will also rely on compaction, but within the delivery cannula to a predefined inner diameter and overall length that also drive the compaction ratio.

Density of the gold wire structures are also varied multidirectionally, such that advancement through pushing via a cannula can be achieved in the lengthwise direction of the structure, but with the structure still maintaining overall flexibility once extruded from the tip of the cannula. Winding around a mandrel with horizontal traversing, as shown in FIGS. 11(a)-11(d), 12(a)-12(d), and 13(a)-13(c).

Figure 22:
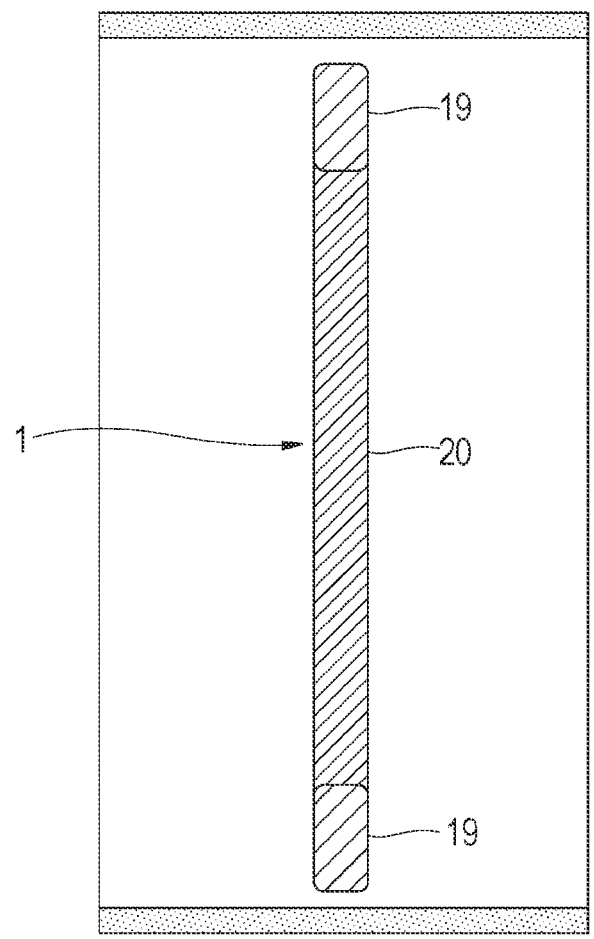
FIG. 22 is a schematic of variable density of a rolled wire structure, with lower compaction ratio areas at either end surrounding a higher compaction ratio area.
Figures 23A, 23B:
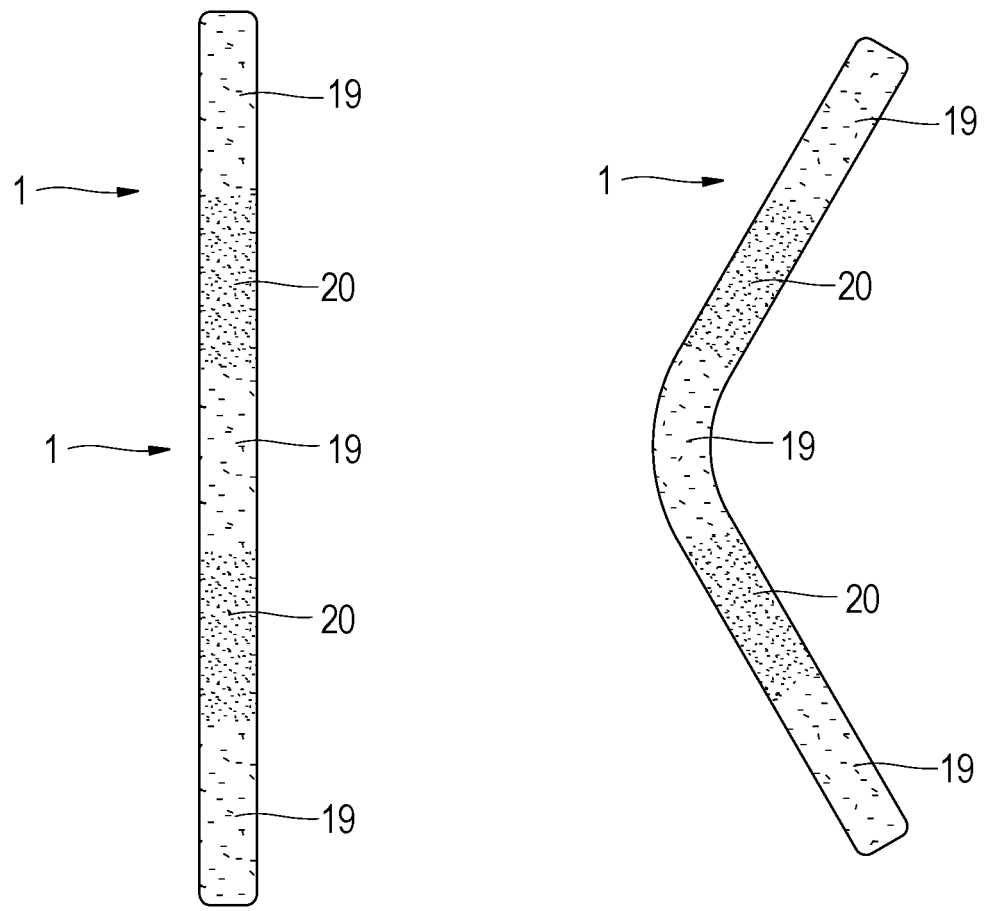
FIG. 23 (a) is a schematic of a wire electrode comprising areas of differing compaction ratio which comprise at least one alternating sequence of areas of higher and lower compaction ratio.

FIG. 22 is a schematic of variable densities of a rolled wire structure 1a, with lower compaction ratio areas 19 at either end surrounding a higher compaction ratio area 20. FIG. 23 (a) is a schematic of a wire electrode comprising areas of differing compaction ratio which comprise at least one alternating sequence of areas of higher and lower compaction ratio 19, 20 allowing said rolled wire structure to bend predictably at the area of lower compaction ratio. FIG. 23 (b) is the same embodiment as in FIG. 23 (a), but the central portion which is of lower compaction ration allows the electrode to bend reliably and predictably at this location. This allows the physician to use this bend to come in close contact with the target tissue on a large portion of the diameter of a peripheral nerve or other tissue.

k. Surface Area

Surface area is quantified for a wire electrode by length of wire and wire diameter-pi ( )*length*diameter. This is because in a porous structure, all of the wire surface is exposed to tissues in the body. By controlling the length of wire deposited within each functional region of the electrode (target, interconnect, subcutaneous interface), the surface area within each region is controlled, thereby controlling the electrode-electrolyte interface area. For example, wire structure electrode consisting only of gold wire that has overall wire length of 10 meters (25 micron diameter) before manufacturing, has a surface area of 785 mm^2. The distribution percentage in one embodiment is 40%-10%-50% (target, interconnect, subcutaneous interface), but may be varied based on the clinician's assessment.

Figure 24A:
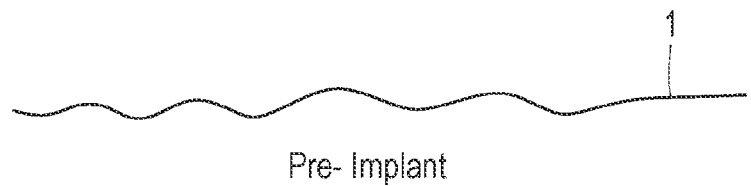
FIGS. 24 (a)-(b) show a distribution of surface area for one embodiment of the rolled wire structure electrode.
Figure 24B:
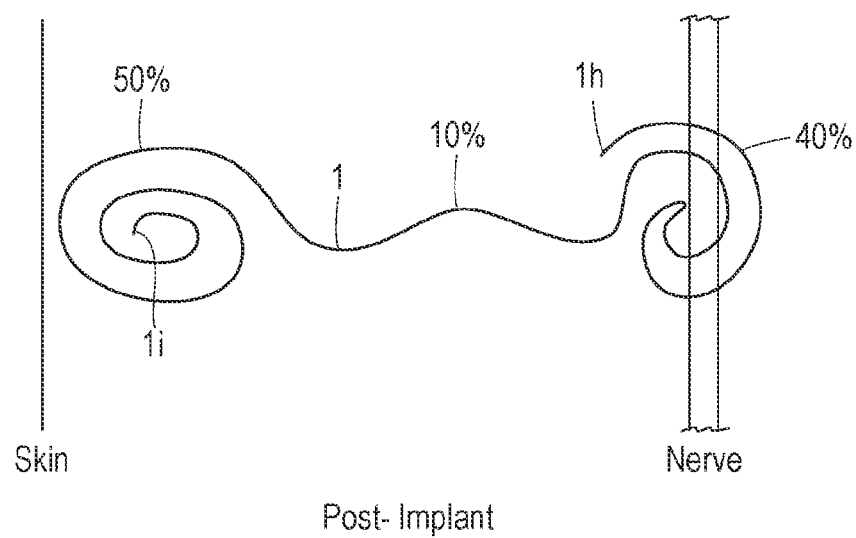

FIG. 24 illustrates the distribution percentage of surface area for one embodiment of a rolled wire structure with a first end 1h injected and bunched at a nerve at 40%, an interconnection area at 10%, and a second end 1i bunched in the subcutaneous region at 50%.

l. Reinforcers to Assist with Bending and Positioning

Figure 25A:
FIG. 25 (a) is a view of a rolled wire structure.
FIGS. 25(b)-(d) show the same structure as FIG. 25(a) with differing patterns of glue or other reinforcers attached.
Figure 25B:
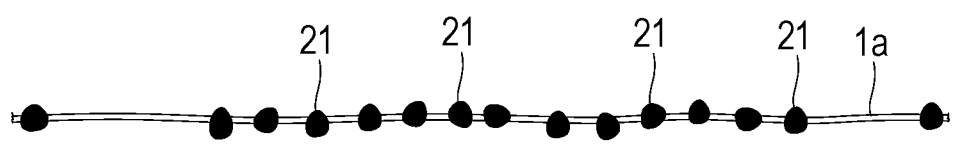
Figure 25C:
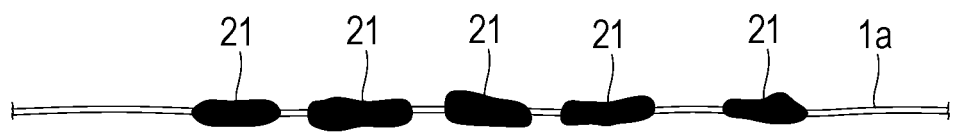
Figure 25D:
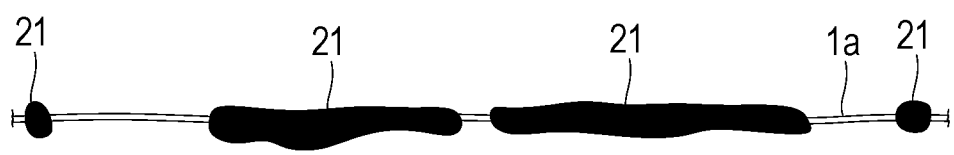

Further, to aid with mechanical stability, additional embodiments of the wire structure may comprise reinforcers placed intermittently along the length of the wire structure. FIG. 25 (a) is a schematic of a rolled wire structure, and 25 (b)-(d) are copies of FIG. 25(a) showing differing patterns of glue or other reinforcers attached. FIG. 25 (a) shows a rolled wire structure base prior to adding medical grade surgical glue or medical grade silicone, the process of adding glue/silicone and hardening is performed ex-vivo so that the glue or silicone does not cure in the body. FIGS. 25 (b)-(d) illustrate how different embodiments may have a reinforcer (e.g., glue or other material adding rigidity) in differing patterns and for different distances of the rolled wire base structure. Note that the roughened and porous surface if of the rolled wire structure is retained at specific points by not having them covered with surgical glue or medical grade silicone to permit sufficient tissue ingrowth at these porous locations, thereby providing for stable chronic mechanical anchoring without the need for permanently placed sutures. In addition to glue or silicone, bits of metal or nonconductive material may be affixed to the wire structure to create intermittent rigidity, as with the glue or silicone.

m. Cannula or Other Delivery Device

The needle may be straight, may have a predetermined curvature or may have an adaptable curvature to it. The extrusion point on the needle may be the needle front colinear with the needle's inner cord line or it may be near the front of the needle on the side of the needle at an angle greater than 0 but less than 90 degrees with respect to the needle's inner cord line (center line).

The wire electrode is flexible and porous but, at sufficient linear density including as described herein, may be injected linearly via a cannula and plunger. The cannula and plunger may be flexible or semi-rigid materials. The cannula may have different tip geometries, like a bending direction, to allow placement of the twisted or braided wire structure in specific manners, locations, or final geometries to interface with target anatomy.

n. In-Body Placement by First Creating a Cavity

An embodiment of the wire structure electrode is extruded only after a cavity 22 has been intentionally formed near or on a tissue target by dissection means such as fluid 34 or a balloon 36. Once the cavity 22 has been created, the wire may be extruded into the cavity partially or fully folding one or multiple times on or around itself, thereby filling the cavity created during the beginning of the injection procedure, adhering to the target tissue.

Figure 26:
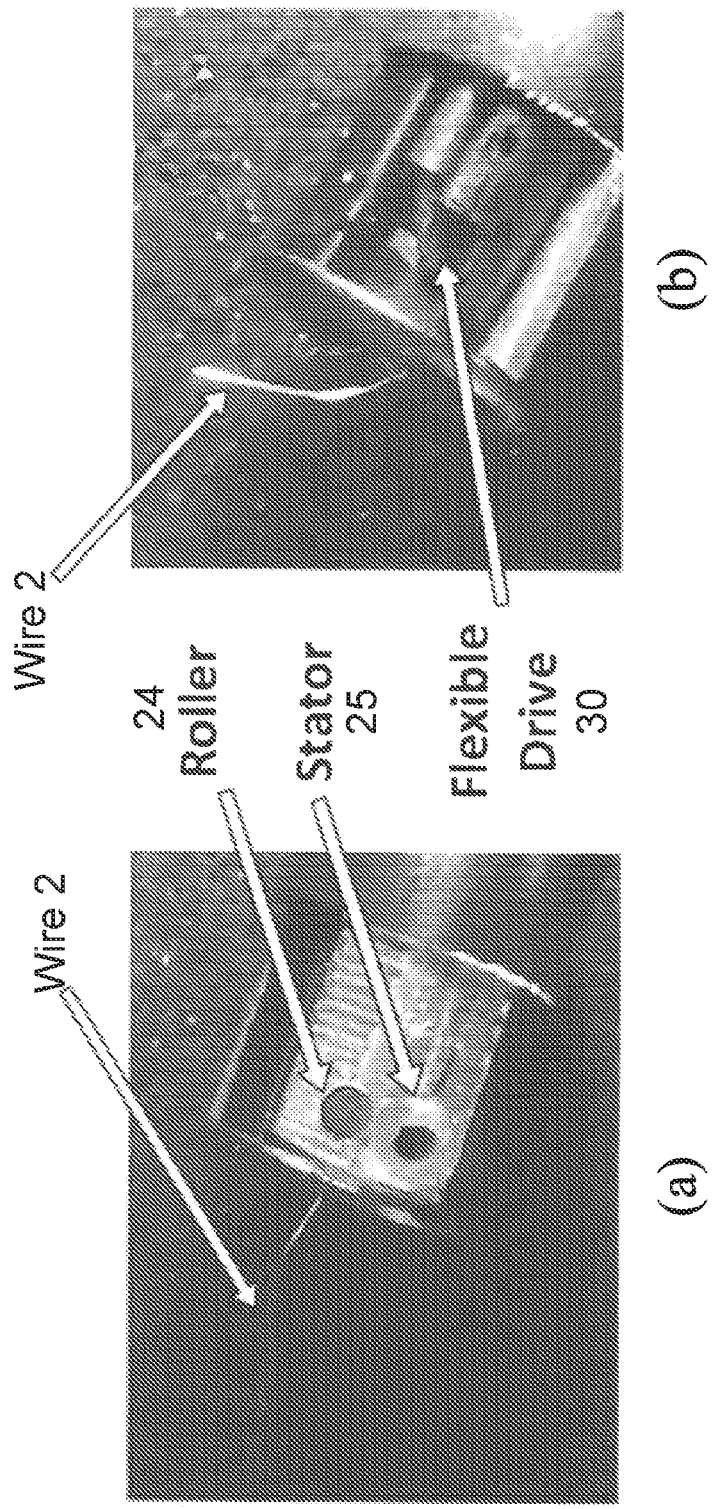
FIGS. 26 (a) and (b) are photographs of opposite sides of the insertion end of a cannula, FIG. 26(a) showing how the roller and stator connect to the side of a housing, and FIG. 26(b) showing the flexible drive for the roller.
Figure 27C:
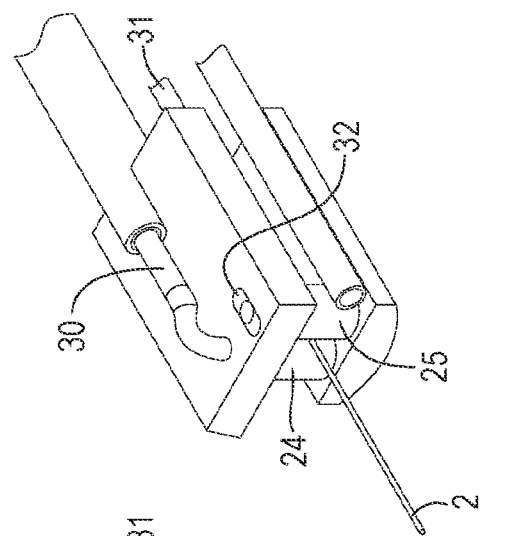
FIG. 27(b) shows a cutaway of the cannula housing revealing the flexible drive and FIG. 27(c) shows the cannula at the insertion end without the housing.
Figure 27B:
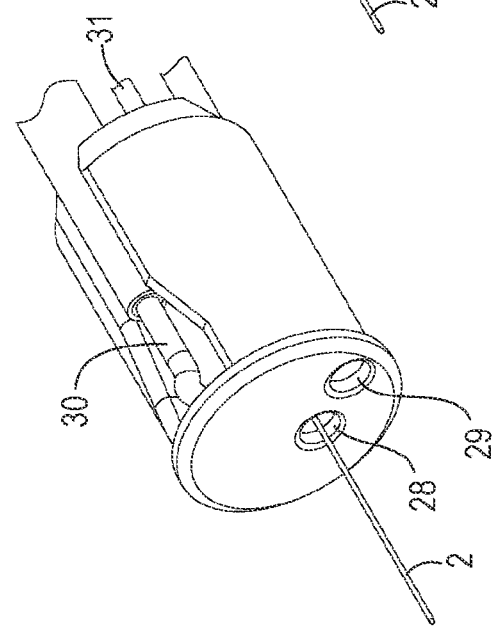
Figure 27A:
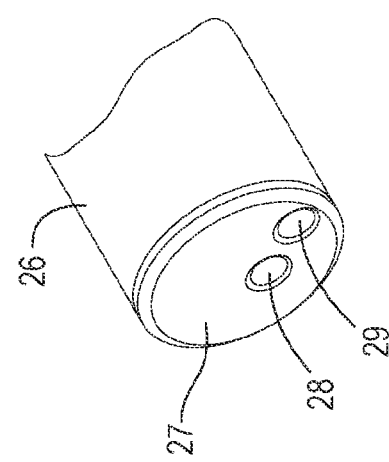
FIG. 27 (a) shows an overall view of a cannula housing at the insertion end with a dissection port, a wire port and an adhesive port.
Figure 28A:
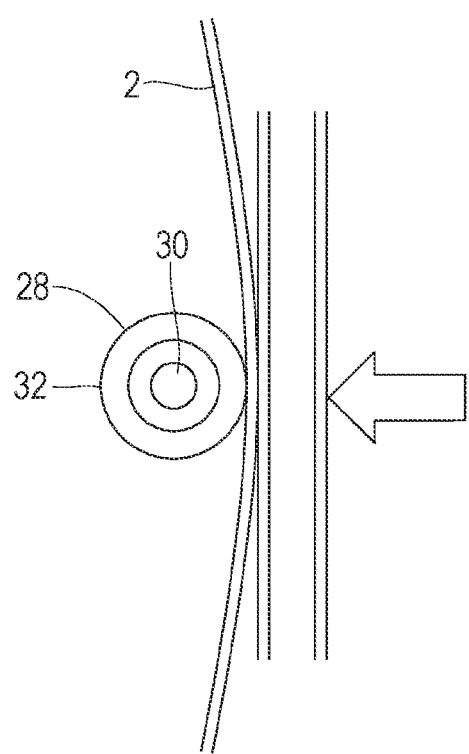
FIGS. 28(a) and 28(b) are schematic views of a roller and stator mechanism for extruding wire from a cannula.
Figure 28B:
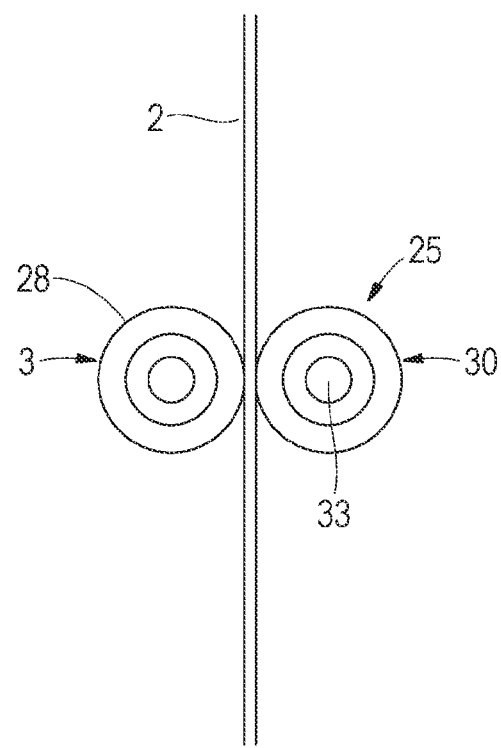
Figure 29:
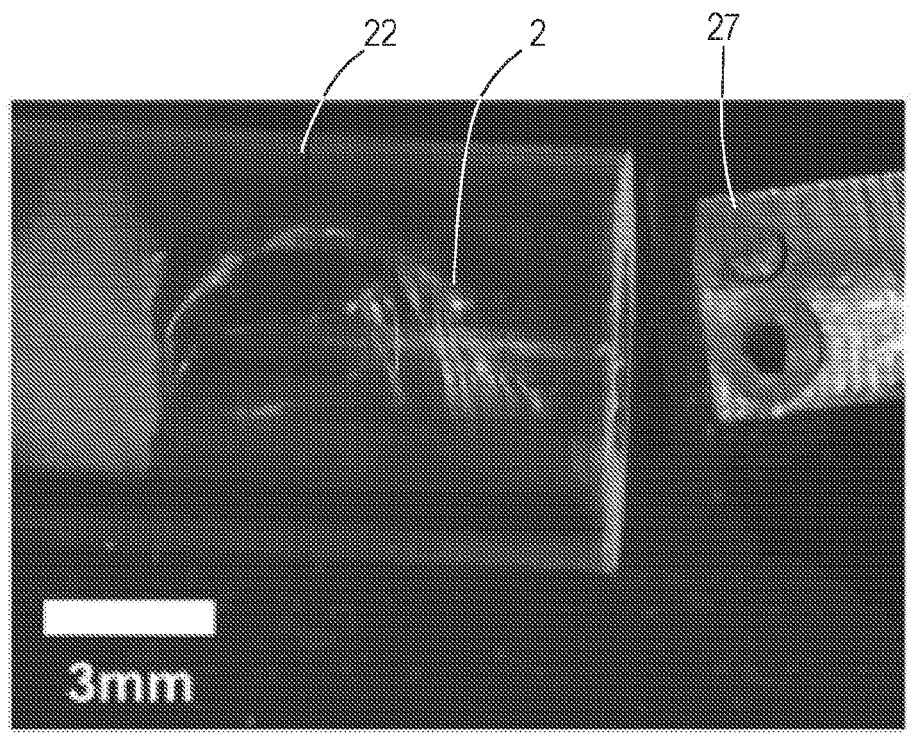
FIG. 29 is a photograph of 25 micron wire extruded into a cavity from a cannula.
Figure 30:
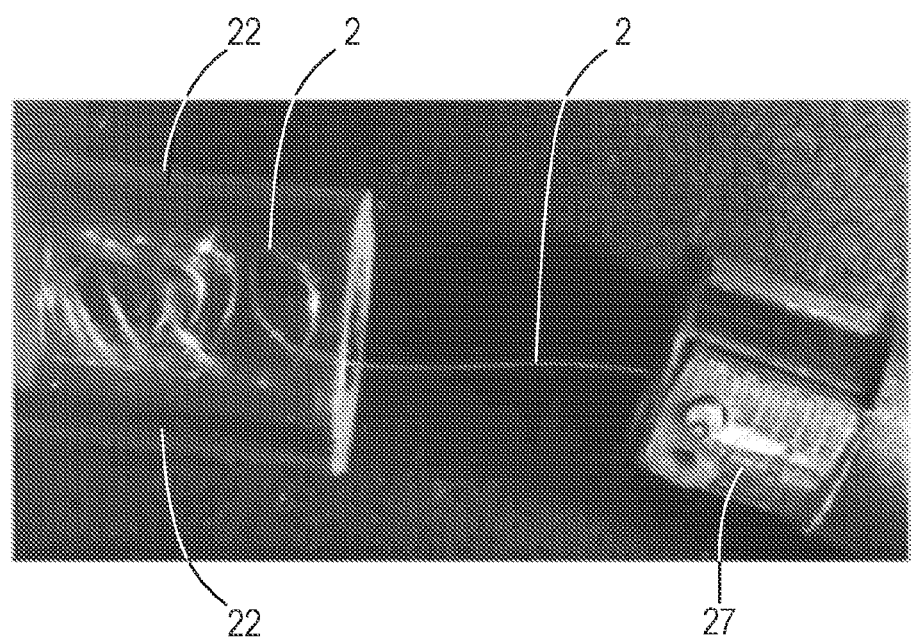
FIG. 30 is a photograph of 100 micron wire extruded into a cavity from a cannula.

FIG. 26 (a)-(b) are photographs of opposite sides of the insertion end 27 of a cannula 23, FIG. 26(a) showing how the roller 24 and stator 25 connect to the side of a housing 26, and FIG. 26(b) showing the flexible drive 30 for the roller 24. FIG. 27(a) shows an overall view of a cannula housing 26 at the insertion end 27 with a dissection port 29 and a wire port 28, FIG. 27(b) shows a cutaway of the cannula housing 26 revealing the flexible drive 30 and FIG. 27 (c) shows the cannula at the insertion end 27 without the housing. FIG. 28 (a)-(b) are schematics of a roller and stator mechanism for extruding wire from a cannula, each comprising a surface and a drive. The arrow in FIG. 28(a) illustrates resistance supplied by the stator 25 to grip the wire 2. The roller surface 30 may be a silicone or similar and the stator surface 30 should be a low friction material such as PTFE or similar. FIG. 29 is a photograph of 25 micron wire extruded into an artificial cavity 22 from a cannula. FIG. 30 is a photograph of 100 micron wire extruded into an artificial cavity 22 from a cannula.

FIG. 31 depicts steps of insertion to a tissue target of one embodiment of a cannula to create an extruded wire structure electrode 1j employing creation of a cavity 22 first before injection of the wire from a wire chamber 31 out of the wire port 28 near the tissue target: FIG. 31(a) insertion end 27 approaches the tissue target 9, FIG. 31(b) dissection means with a fluid 34 such as saline solution from the dissection port 29 creating a cavity 22 near the tissue target 9, FIG. 31(c) wire extrusion starts from the wire port 28 into the cavity 22, FIG. 31(d) wire 2 meanders within the cavity, FIG. 31(e) the cavity 22 is filled with wire at sufficient density to constitute an extruded wire electrode 1j, FIG. 31(f) the insertion end 27 has been retracted and the arrow 5 points toward the continuation of wire extrusion towards the subcutaneous region 8a for connection to power delivery (wire extrusion continues but is not shown in FIG. 31(a)-(f)). The extruded wire structure electrode 1j has been inserted and remains either on or near the tissue target 9.

Figure 32:
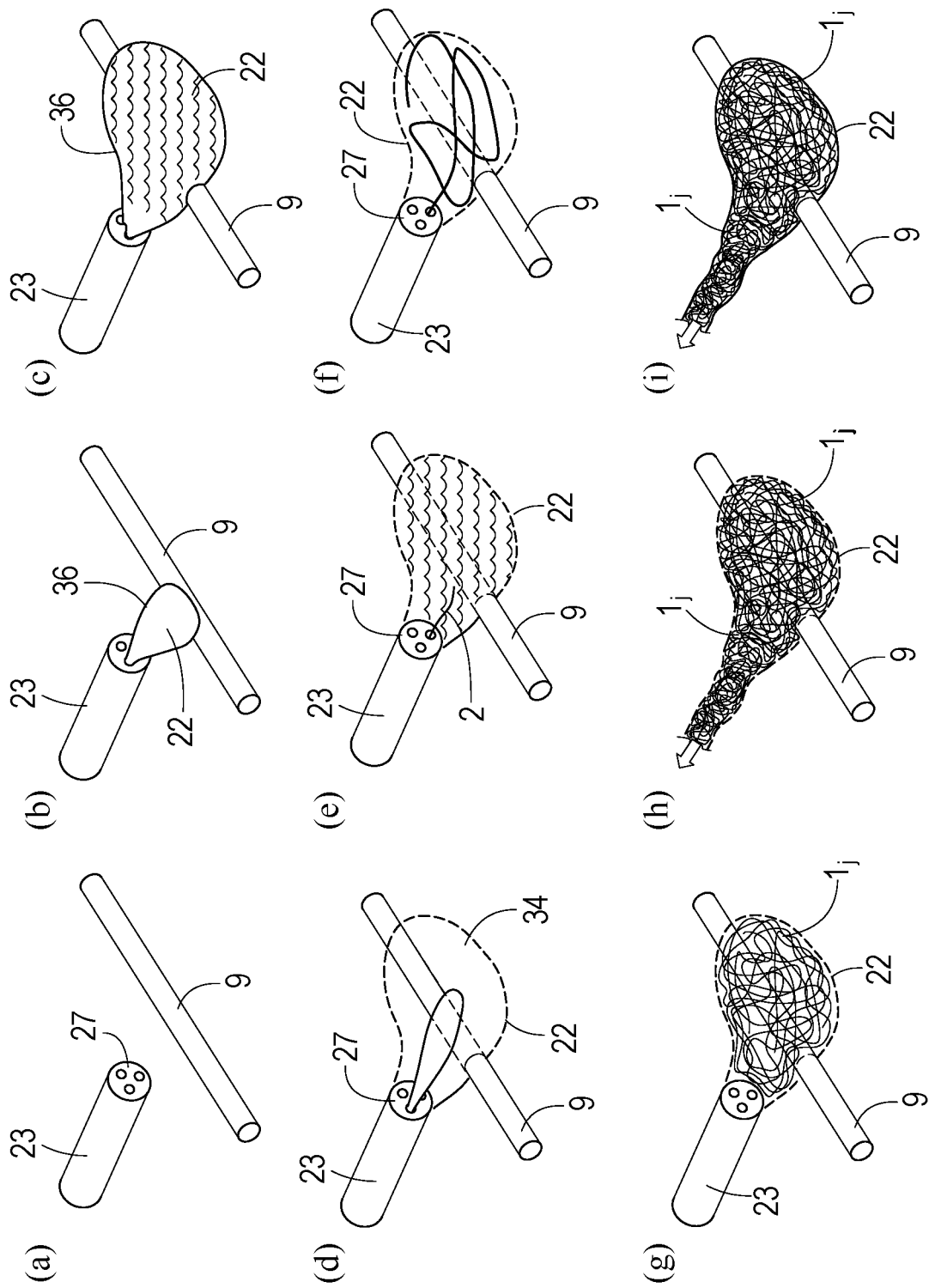
FIGS. 32(a)-32(i) depict steps of injection of one embodiment of a cannula using a balloon as dissection means to extrude an injectable wire electrode, employing creation of a cavity first for the wire near the tissue target.

FIG. 32 depicts steps of injection of one embodiment of a cannula using a balloon as dissection means to extrude a wire electrode employing creation of a cavity first for the wire near the tissue target: FIG. 32(a) approach target nerve with insertion end 27 of the cannula, FIG. 32(b) deploy balloon 36, FIG. 32(c) full deployment of balloon 36 for blunt dissection of cavity 22 above nerve or other tissue target, FIG. 32(d) retraction of balloon 36 and filling of balloon 36 formed cavity 22 with saline 34, FIG. 32(e) injection of wire 2, FIG. 32(f) cavity 22 filling with wire 2, FIG. 32(g) dissected cavity fully filled with wire, FIG. 32(h) retraction of cannula 23 and continuous wire deposition/delivery, and FIG. 32(i) resulting extruded wire structure electrode 1j with arrow pointing to subcutaneous region 8a where this process is repeated to create a collector pad for reception of electrical power.

In one embodiment two or more wires 2 may be extruded from the wire port 28. In another embodiment, a twisted or braided wire structure 1c all of the same material may be extruded. The twisted or braided wire structure may also contain different strands of nonmetallic material (e.g. gold and prolene 10-0 (0.2 mm diameter) or 9-0 (0.3 mm) or nylon 9-0 (0.3 mm), 10-0 (0.2 mm), 11-0 (0.1 mm) or even 12-0 (0.01 to 0.09 mm) diameter, or even stainless steel of 0.02 to 0.2 mm diameter to be in the same range as the gold wire. A rope of skeined wires of same or different materials may be extruded, as well as a rope comprising one central wire with, for example, six same size wires as the center wire, or four slightly larger wires that are larger than the center wire.

The balloon 36 is collapsible and may be deployed via trocar or embedded within the spaghetti shooter. The balloon may be filled with air or with a liquid such as saline to inflate and deflate it in a controlled and predictable way. In this process, the cavity created by the balloon may be filled with saline as the balloon deflates to maintain the cavity shape and allow for free injection of gold wire(s). The balloon may be around the injection needle such that the needle can be pushed at the location the cavity is to be formed, then the balloon is being inflated, later deflated to reveal the cavity prior to slightly pulling the needle back to deploy the electrode from the needle. The extruded wire structure electrode 1j, as a flexible medium/material, may stay in place if a redeployment of the balloon is needed to further stretch the cavity out if it is deemed necessary as long as enough wire electrode is being pushed out of the needle during the needle relocation and balloon inflation to prevent unnecessary movement of the already deployed wire length inside the to be enlarged cavity. Redeployment may be desired when the wire is to be placed on contralateral sides of a nerve to increase material coverage and nerve contact for efficient depolarization. Redeployment under the skin following the placement of the nerve contacting filled cavity and interconnect to the skin, where another cavity will be created and filled with wire. In one embodiment, the balloon 36 is filled with air or with a liquid such as saline to inflate and deflate it in a controlled and predictable way. In one embodiment the balloon 36 surrounds the cannula 23 such that a needle can be pushed at the location where the cavity is to be formed, then the balloon is inflated, and later deflated to reveal the cavity prior to slightly pulling the needle back to deploy the wire from the needle. The wire electrode, as a flexible medium, may stay in place if a redeployment of the balloon is needed to further stretch the cavity out if it is deemed necessary as long as enough wire electrode is being pushed out of the needle during the needle relocation and balloon inflation to prevent unnecessary movement of the already deployed wire electrode length inside the to be enlarged cavity.

o. Power Delivery

Figure 33:
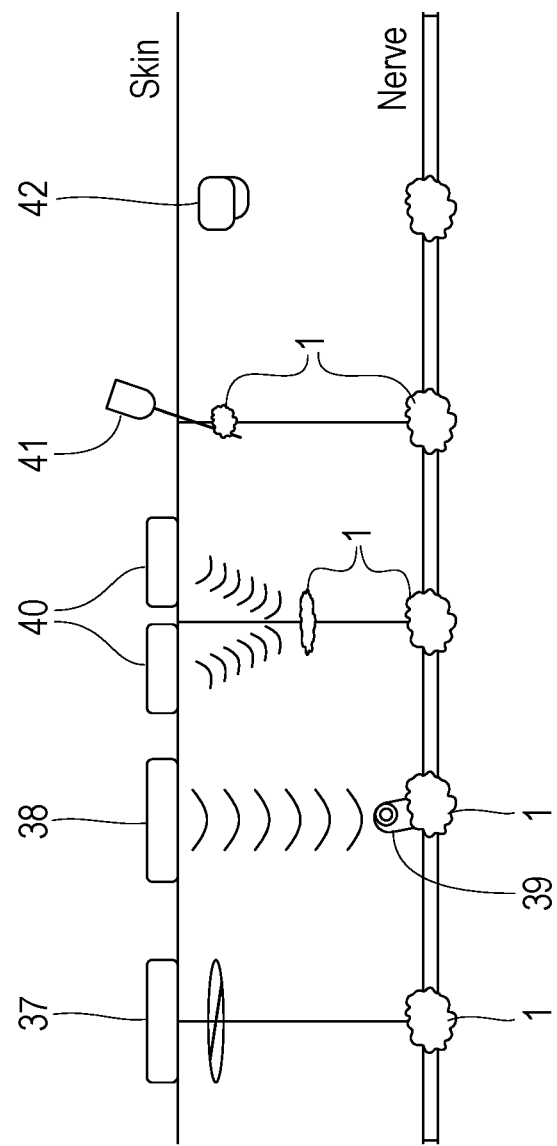
FIG. 33 depicts different means of delivering power to the injectable wire structure electrode.

Power is delivered to the wire structure electrode by various different means as depicted in FIG. 33.

TENS Collector: TENS devices 37 as shown in FIG. 33 deliver a pulsed current between pairs of patch electrodes placed on the skin to activate an underlying nerve. However, surface level stimulation is unreliable for more specific recruitment of targeted nerve fibers. By extruding a wire structure electrode 1 from its targeted tissue to form a collector near the skin's surface, a direct electrical interface can be formed between the wire structure electrode 1 and the patch electrodes of a TENS device 37, which serves as an external generator with modifiable pulse parameters. If necessary, patch electrodes can be modified to incorporate small, thin needles to more effectively connect to the collector. Interfacing efficacy is dependent on pulse amplitude, which in practice is established through a trial and error approach. This is non-invasive to minimally invasive access using off-the-shelf units.

Radiofrequency (RF) Coil: FIG. 33 shows power telemetry in neural stimulation devices can be provided by radiofrequency coupled systems 38. Power transfer is mediated by the inductive coupling between a coaxially positioned transmitter and receiver, wherein an electromagnetic field transmits power across tissue to an implanted receiving antenna 39, which passes variable current to the wire electrode for stimulation. RF-coupling allows the wire structure electrode 1 to be used as a passive device, eliminating the requirement for continuous power from implanted batteries or external generators. Power transfer efficiency and frequency of operation is dependent on the required depth for RF penetration and the receiver antenna geometry, shown as a coil in the figure above. Tissue heating can be a limiting factor in RF power transfer to the device. The advantage is that this is a non-invasive stimulator without internal lead, although the antenna should be placed at, and communicate energy to, the wire structure electrode near the tissue target.

Interferential Current RF: FIG. 33 also shows an Interferential Current RF which is also capable of wireless power transfer across tissue. Interferential units rely on the use of multiple, independent pairs of electrodes 40 oriented to produce amplitude-modulated interference patterns of energy in tissue. Electrode pairs may each receive an AC signal at a different frequency or phase. The resultant "beat frequency" supplied to the wire structure electrode is dependent on the difference in frequency between the two AC signals. Interferential stimulation may allow for more specific, deeper tissue penetration of the signal and a higher resultant amplitude. Advantages are that this method is non-invasive and more specific than TENS or RF alone.

Percutaneous Direct through a microneedle array: FIG. 33 also shows wire structure electrodes 41 with a collector electrode near the skin surface can also be interfaced temporarily through direct interfacing. Effective interfacing, using 27 gauge and smaller needles, is easily achieved. FIG.

33 shows the setup used to interface with subdermal implants of wire structure electrodes, verifying their expected low impedance. This moderately invasive interfacing approach also allows for the greatest current injection capabilities due to low contact impedance between the material and needle.

Implanted Generator (IPG): The alternative to interfacing the Wire structure electrode with externally powered systems is the use of an internalized device to deliver current. The implantable pulse generator (IPG) 42 combines the power source and impulse controller in a programmable, pacemaker-like device, eliminating the patient need for a permanent external attachment. IPGs are typically implanted and sutured into place in a subcutaneous pocket near the targeted nerve, as to prevent the IPG from moving in the pocket. Some benefits of currently available IPGs are rechargeability and capability of controlling up to 16 leads; however, the lifespan of an IPG system is dependent on system usage, stimulation parameters, and choice of power source. The advantage is that no external device is needed with most direct interface.

Embedded Lead: Although not included in the figure is the straightforward interfacing approach of using an embedded lead. Electrode hookup wire, already used in the production of other devices, is also used to provide a direct interface to the wire structure electrode at the tissue target. This approach has a primary application in non-survival research settings, due to the well-established complications, generally related to infection and inflammation, that may arise with the use of a percutaneous lead. The advantage is that it is the simplest solution providing a direct interface.

Figure 34:
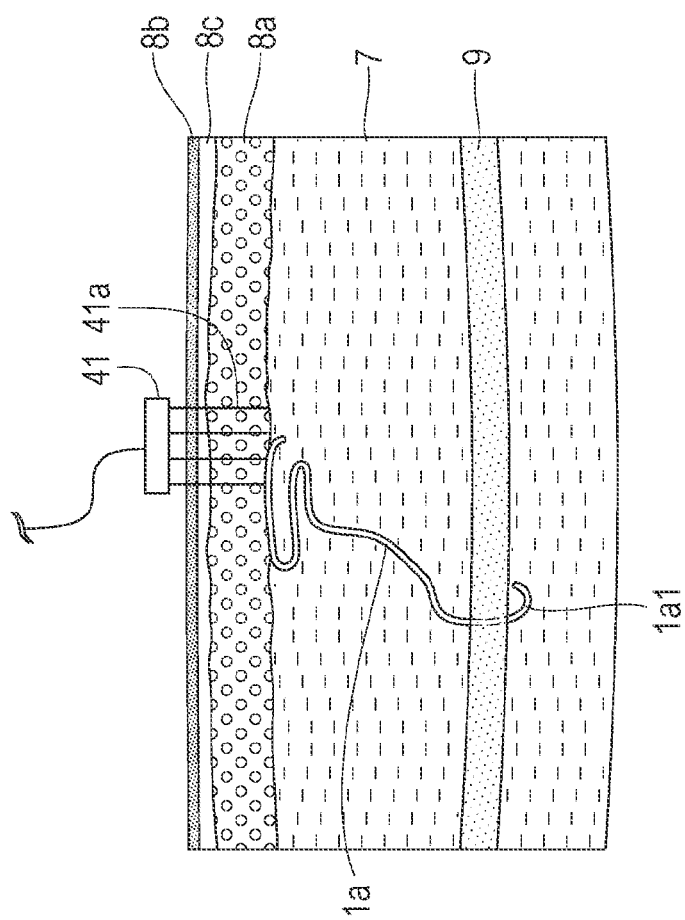
FIG. 34 is a schematic of a section view of skin, muscle and nerve with a microneedle array of a dermal multiplexer piercing the skin and partially contacting a second end of a rolled wire structure in the subcutaneous area, and the first end on or near the target tissue, here a nerve.
Figure 35:
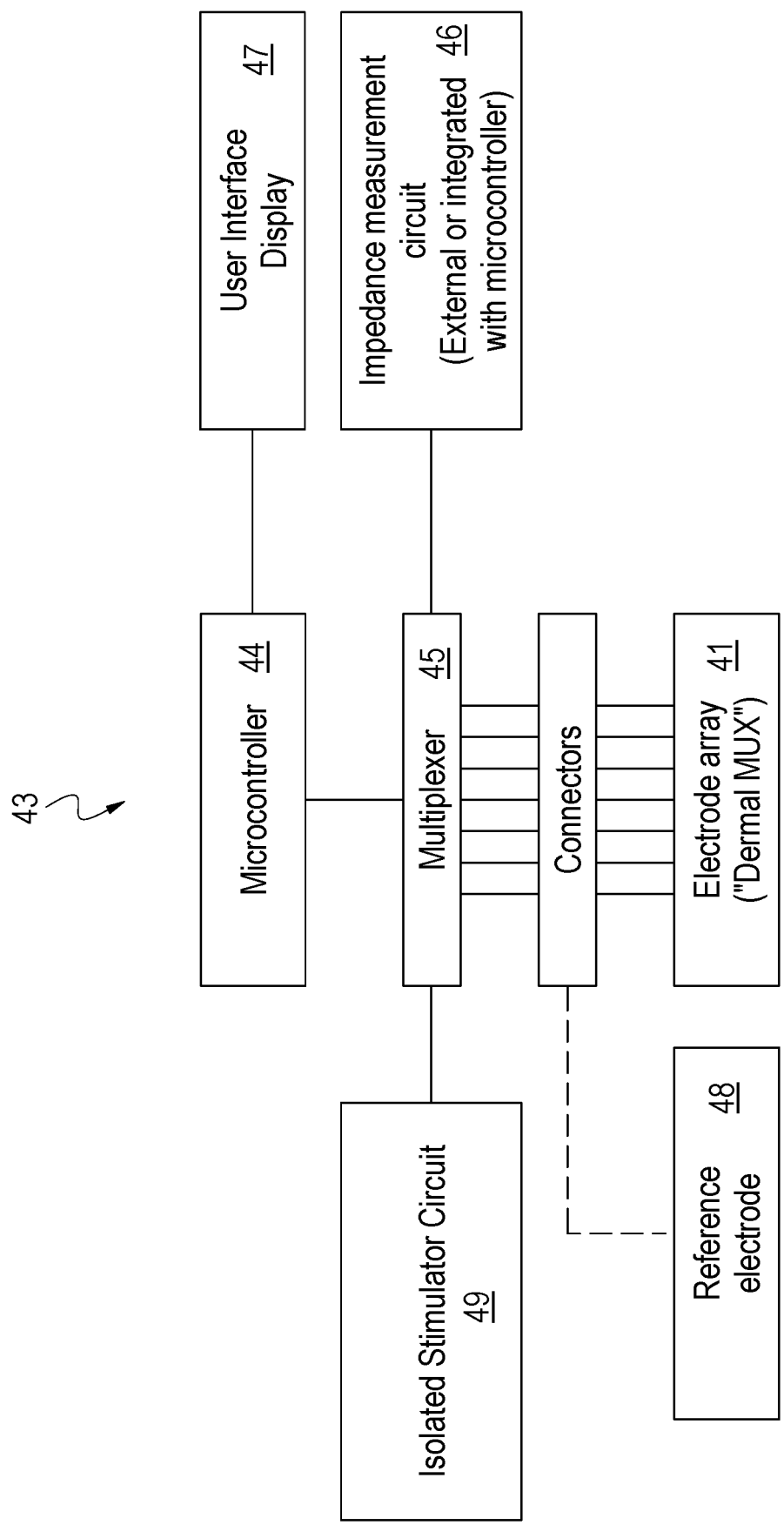
FIG. 35 is a diagram of the components of the dermal multiplexer system.
Figure 36:
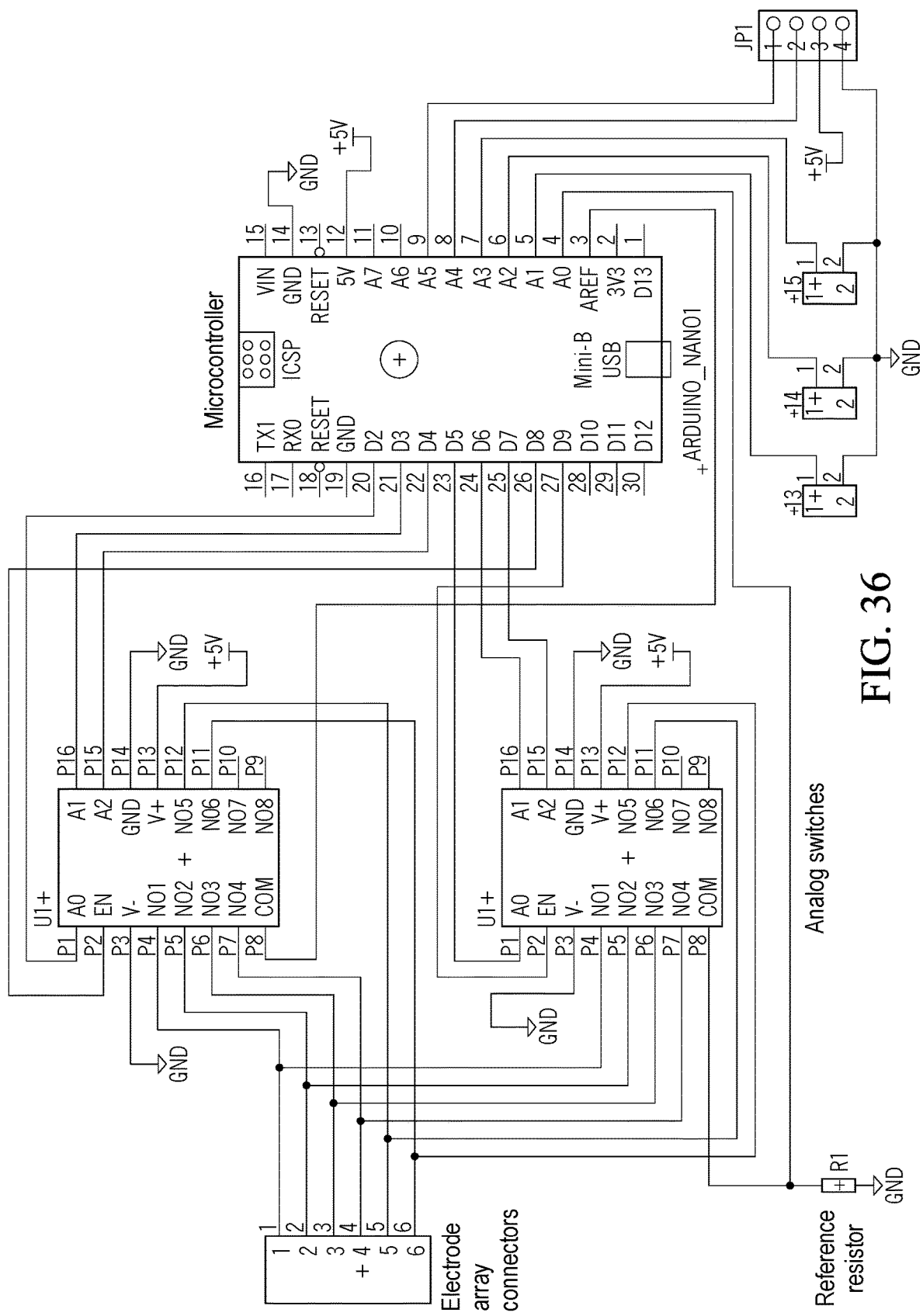
FIG. 36 is a circuit diagram of one embodiment of the dermal multiplexer system including integrated impedance measurement using a simple voltage divider. The circuit with external impedance measurement is similar, with the exception that the voltage divider is removed and an LCR meter is connected to the COM ports of the analog switches (multiplexers).

The percutaneous microneedle array 41 for delivering power percutaneously in one embodiment is part of a dermal multiplexer system. FIG. 34 is a more detailed schematic of a section view of skin, muscle and nerve with a microneedle array 41 of a dermal multiplexer piercing the skin and partially contacting a second end 1*i* of a rolled wire structure in the subcutaneous area 8*a*, and the first end 1*h* on or near the target tissue, here a nerve. FIG. 35 is a diagram of the components of the dermal multiplexer system. FIG. 36 is a circuit diagram of one embodiment of the dermal multiplexer system 43 including integrated impedance measurement using a simple voltage divider. The circuit with external impedance measurement is similar, with the exception that the voltage divider is removed and an LCR meter is connected to the COM ports of the analog switches (multiplexers).

The dermal multiplexer system 43 has a user interface 47 makes a connection to the wire structure electrode in the subcutaneous area 8*a* directly with needles 41*a*. Minimizing needle diameter reduces potential pain to user. The physician or patient should ensure that connection is made reliably (minimizing interfacing coupling impedance) prior to stimulation via the most well-connected needles to the gold wire structure electrode. An isolated stimulator circuit 49 provides electrical current in desired and programmable patterns.

The microneedle array 41 is placed in the vicinity of the wire structure electrode 1*a*, as shown in FIG. 34, and consists of a plurality of microneedles 41*a* spaced to ensure that at least a portion of the microneedles 41*a* make contact with the wire structure electrode. A microcontroller 44 and multiplexers 45 switch between contacts to allow measurement of impedance between several points (pairs of electrodes, or each electrode with an external reference electrode 48). Impedance measurement is achieved by an external LCR unit or an internal voltage divider circuit. Impedance measurement can be either resistive or capacitive, depending on the supplied current waveform. The measurement is made either using an internal impedance measurement circuit 46 or the microcontroller 44 witches pairs of microneedles to be addressed by an external measurement device. Once confirmation of a reliable connection has been established through impedance measurements, stimulation may then be provided via the same multiplexer. The method for percutaneous interfacing with the wire structure electrode using resistive sensing comprises four steps: (1) insert needle array through the skin in the vicinity of the wire structure, (2) deliver sub-stimulation threshold current to a first microneedle 41*a* and measure current through each of the other electrodes; repeat by delivering current to each subsequent electrode, (3) calculate impedance of each pair of microneedles 41*a* to determine which form the best contact with the wire structure electrode under the skin, and (4) stimulate through the needles identified in step 3. The method using capacitive sensing is as follows: (a) insert needle array through the skin in the vicinity of the wire structure electrode, and apply a surface electrode patch to the skin away from the percutaneous electrodes, (b) deliver square-wave pulses at sub-stimulation threshold current through each electrode, and measure current through the surface electrode, (c) Identify which electrode forms the best contact with the wire structure, and (d) stimulate through the identified electrode, with the surface electrode as return.

TENS Dielectric Surface Scanner: An alternative stimulation device based on the TENS principle can be used in place of percutaneous needle arrays. A handheld device uses capacitive sensing to identify the location of the Wire structure electrode as well as to deliver stimulation percutaneously. The device consists of a conductive handle, held by the user, and a skin-facing electrode which the user applies to their skin in the region in which the Wire structure electrode is located. Sub-threshold stimulation is delivered through the skin-facing electrode, using the handle as a return (via the user's hand). Capacitance is measured continuously to identify whether the device is in close proximity to the wire structure electrode under the skin. When the wire structure electrode is detected, the user is alerted by beeping and/or flashing of the device. Stimulation can then be applied percutaneously.

Figure 37:
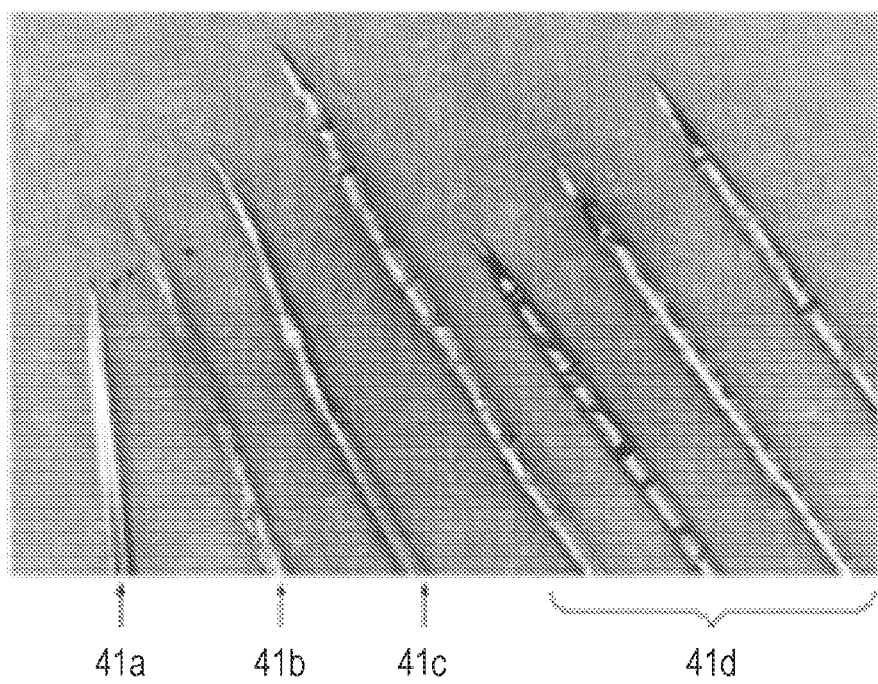
FIG. 37 are images of embodiments of roughened and modified needles for transcutaneous contact with a wire structure electrode.

FIG. 37 is a photo of a needle with standard smooth finish 41*a* (left most) and six needles of modified surface and shape to enable break up of fibrotic tissue around an implanted electrode. Modified needles, from left to right are vertically roughened 41*b*, horizontally roughened and bent 41*c*, and four were indented 41*d*. These modified needles enable percutaneous interfacing electrically with a wire electrode in the subcutaneous or other regions. Roughening may be achieved with a sanding process in a longitudinal or latitudinal direction. Modification of a needle surface acts to remove initial fibrotic layer of cells on the surface of an electrode, reducing impedance and improving the electrical connection.

Figure 38:
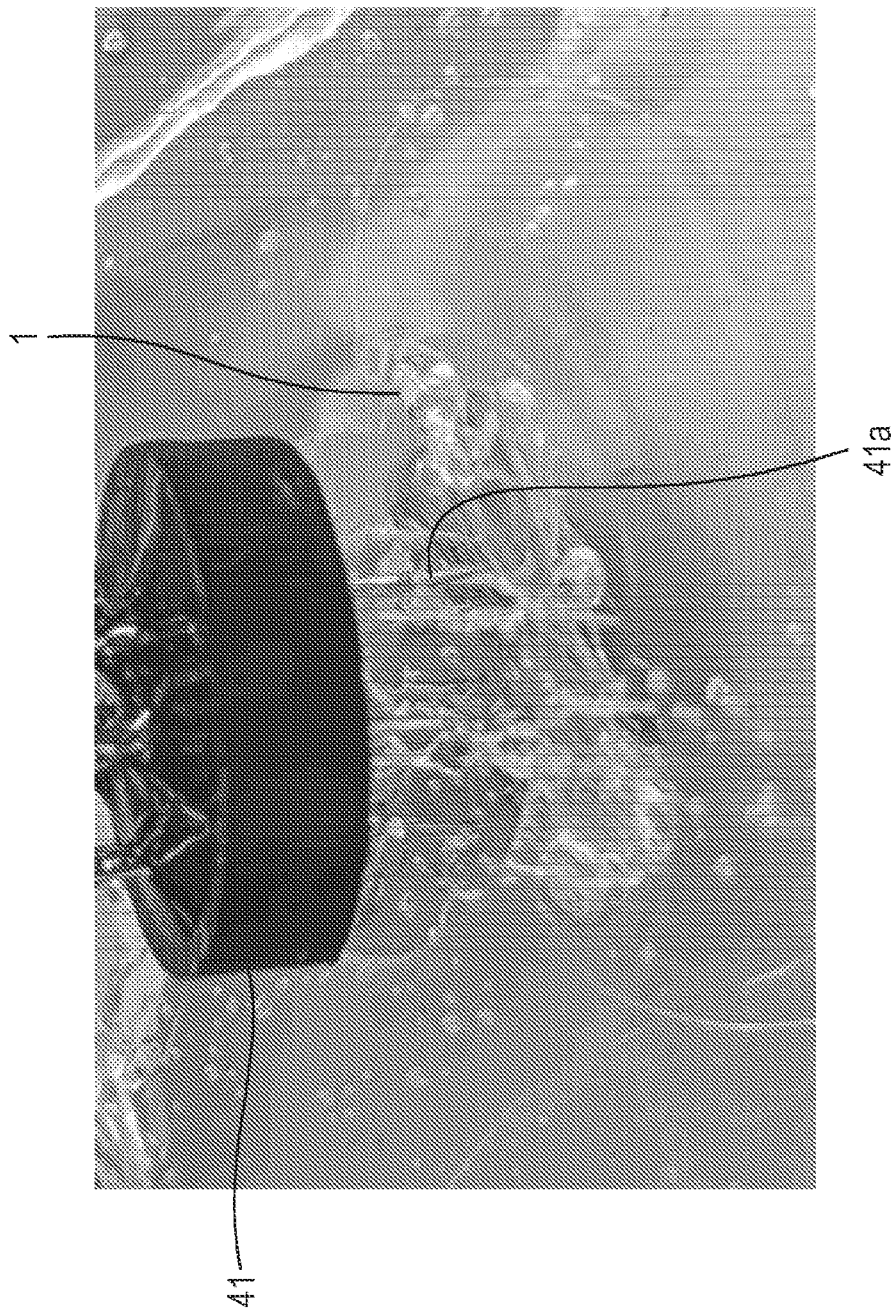
FIG. 38 shows one embodiment of a microneedle array with 30 g needles contacting a wire structure electrode in a ballistics gel benchtop version.
Figure 39:
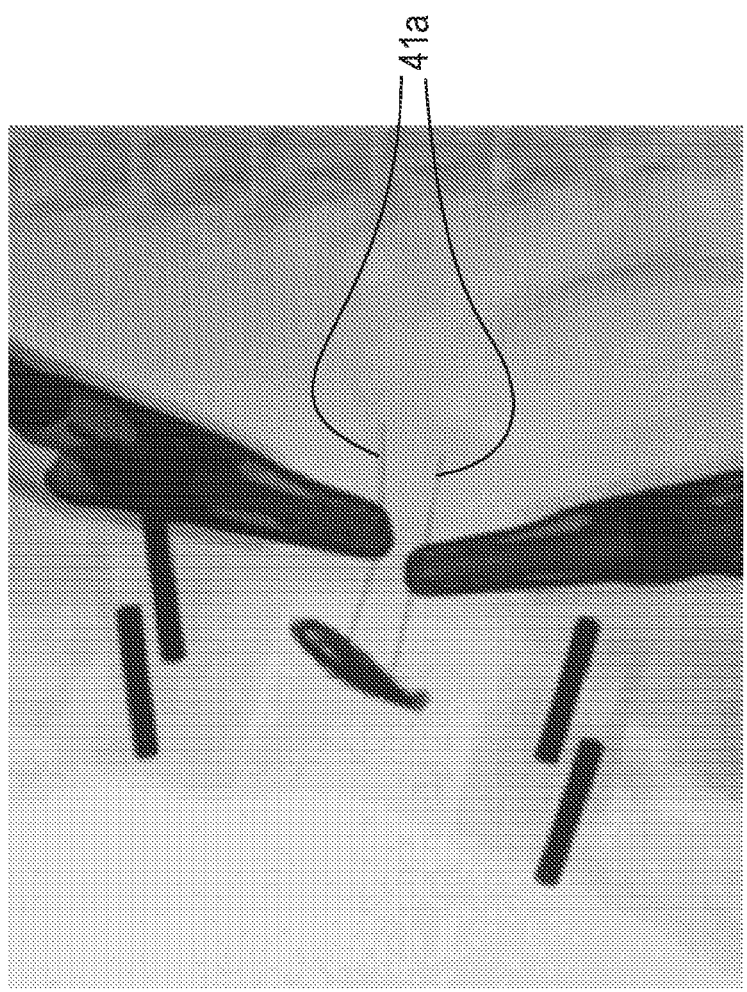
FIG. 39 shows another embodiment of percutaneous power delivery shown under fluoruoscopy with two 30 g needles placed in parallel through a gold wire structure electrode in a rodent model.

FIG. 38 is one embodiment of a microneedle array with 30 g needles contacting a wire structure electrode in a ballistics gel benchtop version. FIG. 39 is another embodiment of percutaneous power delivery shown under fluoroscopy with two 30 g needles placed in parallel through a gold wire structure electrode in a rodent model.

p. Removal or Explant

Where applicable, the ability to explant the Electrode post chronic in-growth of cells and tissues with minimal damage to the supporting cells, tissues and bodily structures such as blood vessels, in some cases with the application of ultrasound and/or other forms of energy prior or during the explantation procedure.

Figure 40:
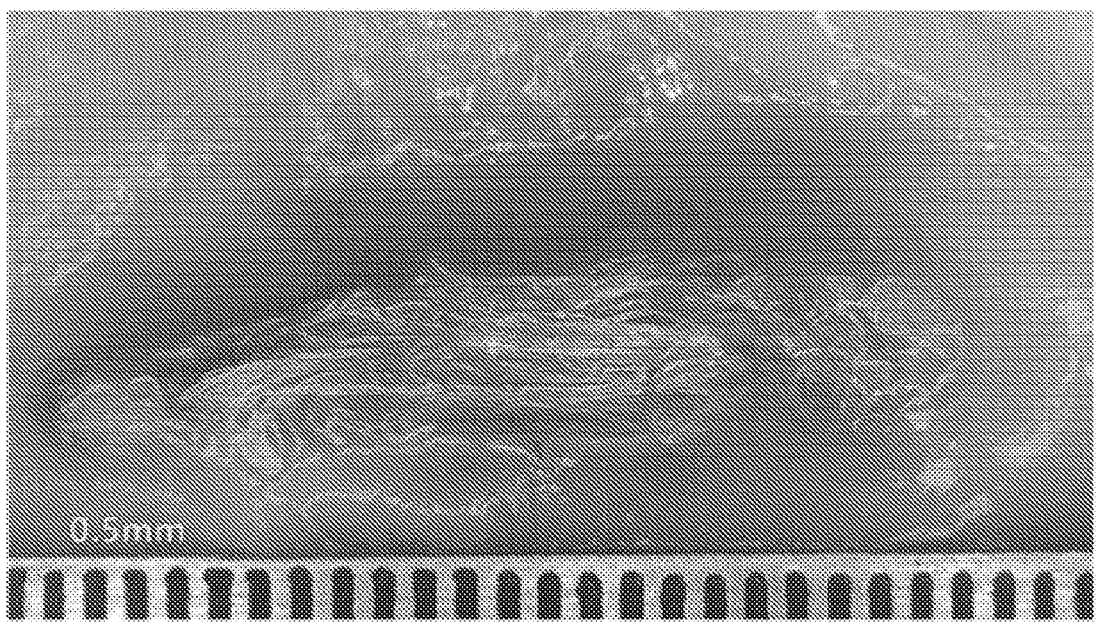
FIG. 40 is a photograph of a folded wire structure comprising 25 micron gold wire upon explant after 60 days subcutaneous in a rodent preclinical model.
Figure 41:
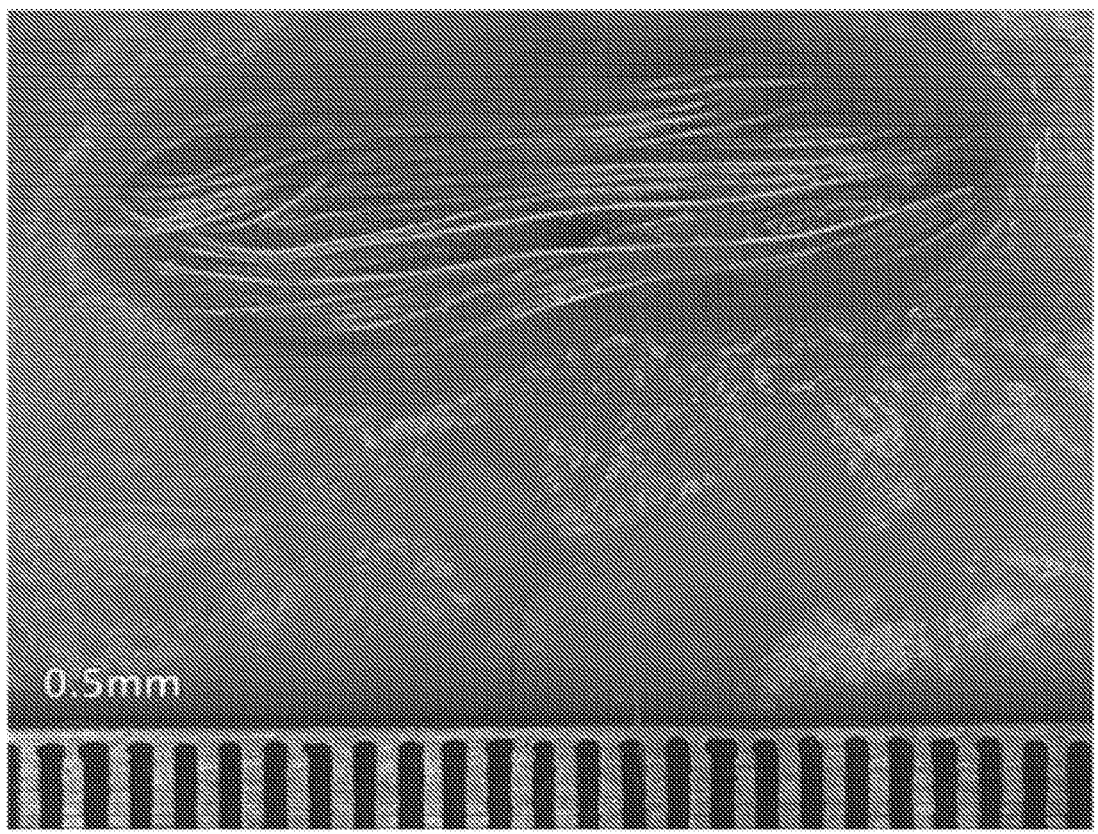
FIG. 41 is a photograph of a folded wire structure comprising 100 micron gold wire upon explant after 60 days subcutaneous in a rodent preclinical model.

Surgical removal of the device in a survival procedure (4 weeks placed, removed, 4-8 weeks survival) has also been completed for devices, also without any adverse events. FIG. 40 is a photograph of 25 micron gold folded wire structure upon explant after 60 days subcutaneous in a rodent preclinical model. FIG. 41 is a photograph of a 100 micron gold wire folded wire structure upon explant after 60 days subcutaneous in a rodent preclinical model.

Generally, the wire structure electrodes made ex-vivo as described herein allow for determined mechanical parameters that can be tested outside of the body to a certain degree that is larger than the in-body cured electrodes.

The ex-vivo manufacturing of the wire structures does not preclude them from being formed in-vivo into their final shape, such as by folding, meandering, spiraling, and thereby occupying a larger volume than the diameter of the delivery device, but only a slightly smaller volume than the cavity created in the body right before the deployment step. It is the intrinsic mechanical stability of the wire structure electrode that allows for an easier removal of the electrode by mechanically pulling on the overall structure, either continuously or in a pulsatile fashion to first dislodge the electrode from the surrounding encapsulation tissue and then carefully pulling it out from the surrounding encapsulation channel.

Additional Embodiments a. Method of Ex Vivo Manufacturing a Folded Wire Structure Electrode In one embodiment the wire-based electrode is a folded wire structure which is manufactured to be injected near a tissue target inside a body. In one embodiment, an ex vivo method of manufacturing the folded wire structure for implantation near a tissue target inside a body, comprising providing at least one highly conductive wire, wrapping at least one highly conductive wire around at least one mandrel outside the body to produce spools comprising two ends and compacting the spools to a folded wire structure not exceeding several mm in diameter and, in one embodiment, and not exceeding 3 mm having voids and a roughened and porous surface. The diameter for the folded wire structure can be matched to the inside diameter of the cannula of the delivery device (e.g., cannula of a syringe). The method may also comprise the additional step of wrapping the at least one highly conductive wire around the at least one mandrel at different speeds so that the spools comprise at least one area of higher compaction ratio and at least one area of lower compaction ratio. In one embodiment the at least one area of lower compaction ratio is located near at least one of the two ends. In one embodiment the at least one area of lower compaction ratio is less than 30% and, in another embodiment, the at least one area of higher compaction ratio at least 30% but less than 60%. The ex vivo method, in another embodiment, the at least one highly conductive wire comprises a plurality of highly conductive wires twisted or braided into a rope. An additional (and optional) step includes twisting the folded wire structure. The method of manufacturing ex vivo may further comprise providing a plurality of wires twisted or braided to form a rope so that the at least one highly conductive wire comprises a plurality of highly conductive wires twisted into a rope. This method may further comprise affixing at least one reinforcer in a specific region of the folded wire structure a wherein the at least one reinforcer comprises a cyanoacrylate material selected from the group consisting of n-butyl cyanoacrylate and 2-octyl cyanoacrylate, a silicone and/ore a length of rigid material.

b. Method of Injecting a Folded Wire Structure Electrode

One method of injecting a folded wire structure, as described herein, near a tissue target in a body, in one embodiment, comprises providing a delivery device comprising a cannula loaded with a folded wire structure comprising at least one highly conductive wire, said folded wire structure comprising a first end and a second end, injecting the first end of the folded wire structure near the tissue target, continuing to inject the folded wire structure while pulling back the cannula from the tissue target so that the second end is expelled from the cannula in a subcutaneous area of the body. Or, in another embodiment, a method of injecting the folded wire structure in a subcutaneous region comprises, providing a syringe comprising a cannula loaded with a folded wire structure comprising at least one highly conductive wire, said folded wire structure comprising a first end and a second end, and injecting the first end of the folded wire structure in a subcutaneous area.

c. Method of Ex Vivo Manufacturing a Rolled Wire Structure Electrode

Disclosed also is another method of manufacturing the rolled wire based electrode for injection near a target tissue inside a body, which can be manufactured ex vivo by a method comprising the steps of providing at least one highly conductive wire, wrapping the at least one highly conductive wire around at least one mandrel outside the body to produce spools comprising two ends, flattening the spools, and rolling the flattened spools, such that the folded wire structure is configured for injection near the tissue target. The method may further comprise providing at least one non-metallic strand, and wrapping said at least one nonmetallic strand around said at least one mandrel.

Optionally the above steps further comprise wrapping the at least one highly conductive wire around the at least one mandrel outside the body at different speeds so that the spools comprise areas of differing areas of compaction ratio and further the differing compaction ratio comprise at least one alternating sequence of areas of higher and lower compaction ratio allowing said rolled wire structure to bend predictably at said area of lower compaction ratio.

In another embodiment, the step of rolling the spools further comprise rolling the flattened spools around a guide wire. In yet another embodiment, without the guide wire, the folded wire structure has a hollow core. In the latter embodiment, the at least one area of lower compaction ratio is located near at least one of the two ends and in another the at least one area of lower compaction ratio is less than 30%. In another embodiment, the at least one area of higher compaction ratio at least 30 but does not exceed 60%. In another, after the folded wire structure has been formed, the folded wire structure may be twisted or twirled. Further, the step of providing at least one highly conductive wire comprises providing a plurality of wires twisted or braided to form a rope so that the at least one highly conductive wire comprises a plurality of wires twisted into a rope. The ex vivo method of claim 1 further comprising step e of adding at least one reinforcer located in a specific region of the wire electrode, said reinforcer selected from the group consisting of, a cyanoacrylate material selected from the group consisting of n-butyl cyanoacrylate and 2-octyl cyanoacrylate, a silicone and/or a length of rigid material.

d. Method of Ex Vivo Manufacturing a Rolled Wire Structure Electrode from Wire Mesh An alternate to the above methods of wrapping at least one highly conductive wire into spools described herein and then flattening and rolling the flattened spools, an ex vivo method of manufacturing a spooled mesh for injection is disclosed comprising providing a mesh comprising at least one highly conductive wire, and rolling the mesh into a spooled mesh, such that the spooled mesh is configured for injection near the tissue target. All other aspects of manufacturing the folded wire structure are incorporated into this method and embodiments.

e. Method of Injecting a Rolled Wire Structure Electrode

Also disclosed is a method of injecting a rolled wire structure electrode for near a tissue target in a body, comprising providing a syringe comprising a cannula loaded with a folded wire structure comprising at least one highly conductive wire, said folded wire structure comprising a first end and a second end, injecting the first end of the folded wire structure near the tissue target, and continuing to inject the folded wire structure so that the second end is extruded from the cannula in a subcutaneous area of the body. The method further comprises at least one area of lower compaction ratio allowing said rolled wire structure to bend reliably, and/or comprises at least one reinforcer located in a specific region of the rolled wire structure and wherein the reinforcer consists of a cyanoacrylate, a silicone, or a length of another rigid material.

In another embodiment, the at least one highly conductive wire comprises a plurality of highly conductive wires twisted into a rope. In another, a guide wire is located in a center of the folded wire structure. In one embodiment, at least one of the first end and second end is bunched. In another embodiment, the method includes bunching the first end near the tissue target and/or the second end in the subcutaneous area.

f. Device for Injecting a Wire Electrode Near a Tissue Target

One device for creating a cavity in a tissue and injecting a rolled wire electrode near a target tissue in a body, comprises a cannula comprising an insertion end and a second end, said cannula further comprising dissection means ending in a dissection port at the insertion end, and a wire delivery line ending in a wire port at the insertion end, said wire delivery line comprising a wire chamber for advancing at least one wire to the wire port, a roller and a stator in contact with the wire, said roller connected to a drive and configured to advance the at least one wire to the wire port, and a controller communicating with the dissection means and the wire delivery line, said controller configured to send commands to the dissection means, advancing wire through the wire port. In another, said dissection means further comprising a balloon housed inside a dissection port, said balloon communicating with said controller and configured with a driver to project from said balloon port and create a cavity near the tissue target, and dissection means also comprising a fluid line configured for fluid dissection and said driver may be connected to a controller configured to create a cavity of a pre-programmed or a custom size, and said fluid comprises at least one of the following selected from the group consisting of an immunoreactive agent, an anti-inflammatory agent, a hemostatic agent, a pharmacological agent and a contrast agent.

g. Method for Injecting an Extruded Wire Electrode Near a Tissue Target

One method for creating a cavity and injecting a wire electrode near a tissue target in a body, comprises placing an insertion end of a cannula into a body near a tissue target, then dissecting tissue surrounding the tissue target with means for dissection at the insertion end to create a cavity around the tissue target, then advancing at least one wire from a wire port at the insertion end into the cavity, and filling the cavity with wire folded in interconnecting loops which contact the tissue target. The means for dissection further comprises a fluid stream from a fluid port or a balloon housed in a balloon port and configured to project outside the balloon port, or any other suitable means. The method herein may also optionally comprise an additional step of introducing a curable glue into voids in the interconnecting loops.

h. System Including a Rolled Wire Structure Electrode

One system for providing energy to a tissue target in a body comprises at least one rolled wire structure manufactured ex vivo and configured for placement near, around, or through the tissue target, said rolled wire structure having first and second ends and comprising at least one highly conductive wire, and comprising a roughened and porous surface, and comprising primary loops in a bulk shape, and secondary loops outside the bulk shape. Further, said first end is configured for injection near the tissue target and said second end configured for implantation in a subcutaneous area, a power source, a power delivery connected to said power source, said power delivery configured to transmit power through the skin to the subcutaneous area, and a controller communicating with the power source. In one embodiment said first end is configured for bunching near the tissue target and said second end is configured for bunching in the subcutaneous tissue. In other embodiments said at least one highly conductive wire comprises a material selected from the group consisting of gold, Platinum, Stainless Steel, Titanium, Iridium, Tungsten and Metal alloys such as MP35N, and may further comprise a coating described in this specification and/or a portion may comprise insulation. In another embodiment the at least one highly conductive wire exceeds one meter in length. The energy source supplies electric current, thermal or electromagnetic energy. The system as in claim 1 wherein said at least one rolled wire structure is configured to maintain conductivity when stretched up to three times of its length or width during normal use in the body. The novel use of highly conductive wire as herein means that the at least one rolled wire structure is configured to be deformable, crushable, spongy, and stretchable and yet maintain conductivity during normal use in the body, resulting in said at least one rolled wire structure after placement in the body having sufficient slack between the first and second ends to maintain conductivity while withstanding normal movement of the body. In one embodiment, at least one rolled wire structure is configured to be placed near the tissue target through a needle. The novel construction means that said at least one rolled wire structure further comprises voids. Other embodiments of the system are that the spools comprise areas of differing compaction ratios, including alternating sequences of the same, and at least one area of higher compaction ratio is at least 30% but does not exceed 60% and at least one area of lower compaction ratio less than 30%, and the at least one area of lower compaction ratio is located near at least one of the two ends. Intermingled with said at least one rolled wire structure in several embodiments are:

at least one immunoreactive agent selected from a group consisting of cells, whole blood, blood serum, biodegradable polymers sugars, amino acids, proteins, iron, lipopolysaccharides, collagen and hyaluronic acid.

at least one anti-inflammatory agent selected from a group consisting of steroids, anti-oxidants, superoxide dismutase mimetics and non-steroidal anti-inflammatory drugs.
at least one hemostatic agent selected from a group consisting of microfibrillar collagen hemostat, chitosan, kaolin, zeolite, anhydrous aluminum and sulfate.
at least one folded wire structure in another embodiment is at least one pharmacological agent selected from a group consisting of an antibiotic, an anti-fungal, an analgesic and an anesthetic.
At least one contrast agent for visualization during ultrasound, fluoroscopy or x-ray selected from a group consisting of fluroscein and platinum.

In another embodiment of the system, said at least one highly conductive wire comprises at least two highly conductive wires having different properties selected from the group consisting of diameter, impedance, flexibility, strength, radio-opacity. In other embodiments of the system, prior to placement in the body, a guide wire is embedded within said at least one rolled wire structure, said guide wire being configured to be removed from the at least one rolled wire structure after placement, and optionally said guide wire is pre-bent or comprises a shape-memory.

The power delivery for the system, in different embodiments, may comprise a TENS unit or, transdermal multiplexer comprising a microcontroller connected to a transdermal electrode array comprising a plurality of microneedles configured to contact said second end of the at least one rolled wire structure, such that electric current flows from said microneedles to said second end, said multiplexer communicating with a measurement circuit for impedance, pulse width and/or frequency, so that the multiplexer directs current to a subset of said microneedles contacting the second end of the rolled wire structure.

The dimensions of said at least one rolled wire structure include a length of 10-1000 mm and 0.5-3.0 mm in outer diameter. In one embodiment, said at least one rolled wire structure comprises an inner hollow channel. In another embodiment said at least one rolled wire structure is intermingled with a cured hydrogel.

An additional embodiment includes a reinforcer affixed intermittently to the rolled wire structure, consisting of materials described elsewhere herein.

The rolled wire structure may be configured to be removable in one piece by a physician using forceps.

i. Method of Suture-Less Integration of a Rolled Wire Structure Electrode into a Bodily Tissue The rolled wire structure may provide a way to anchor it on or near a tissue target. Disclosed herein is a method of suture-less integration of a rolled wire structure near a target tissue in a body which, in one embodiment, comprises the step of providing a rolled wire structure in a delivery device, said rolled wire structure comprising overlapping loops and voids, in a bulk shape comprising primary loops and a roughened surface from which secondary loops extend, and the additional step of injecting the rolled wire structure through skin of the body to a location near the target tissue, and the step of allowing ingrowth of cellular and vascular tissue of the body into said voids of the rolled wire structure, such that said cellular and vascular tissue secures the rolled wire structure near the target tissue. Optionally, in another embodiment, the step of providing a rolled wire structure in a delivery device further comprises said rolled wire structure being intermingled with a quantity of at least one pro-angiogenic agent selected from the group consisting of vascular endothelial growth factor, fibroblast growth factor-2, platelet derived growth factor, and platelet derived endothelial cell growth factor/thymidine phosphorylase. Further, an additional embodiment comprises adding, between the steps of providing and inject, an additional step of creating a cavity near the target tissue with said delivery device.

j. Method of Suture-Less Integration of a Folded Wire Structure into a Bodily Tissue The folded wire structure electrode may provide a way to anchor it on or near a tissue target. Disclosed herein is a method of suture-less integration of a folded wire structure near a target tissue in a body which, in one embodiment, comprises the step of providing a folded wire structure in a delivery device, said folded wire structure comprising overlapping loops and voids in a bulk shape comprising a roughened surface, and loops protruding from said roughened surface of said bulk shape, and the additional step of injecting the folded wire structure through skin of the body to a location near the target tissue, and the step of allowing ingrowth of cellular and vascular tissue of the body into said voids of the folded wire structure, such that said cellular and vascular tissue secures the folded wire structure near the target tissue. Optionally, in another embodiment, the step of providing a folded wire structure in a delivery device further comprises said folded wire structure being intermingled with a quantity of at least one pro-angiogenic agent selected from the group consisting of vascular endothelial growth factor, fibroblast growth factor-2, platelet derived growth factor, and platelet derived endothelial cell growth factor/thymidine phosphorylase. Further, an additional embodiment comprises adding, between the steps of providing and inject, an additional step of creating a cavity near the target tissue with said delivery device.

k. Wire Electrode

An injectable wire structure electrode may comprise at least one highly conductive and biocompatible wires compacted into primary loops and/or folds, said loops and said folds with voids comprising a bulk shape comprising a roughened and porous surface and secondary loops protruding from said roughened and porous surface of said bulk shape, such that said primary and secondary loops and folds are in contact with surrounding tissue providing a continuous pathway for conduction of energy, said wire electrode and having at least one compaction ratio. In one embodiment of the injectable wire electrode, at least a portion of the plurality of highly conductive and biocompatible wires are twisted or braided rope-like structures. The plurality of wires in one embodiment comprise different diameters and/or materials and/or surface coatings, and the device may further comprise nonmetallic strands of material. The wire structure electrode comprises areas of differing compaction ratios which, in one embodiment, comprise at least one alternating sequence of areas of higher and lower compaction ratios allowing said wire electrode to bend predictably at said area of lower compaction ratio. In one embodiment the wire electrode further comprises a first end for placement near a target tissue in a body, and a second end for placement near or on a power source. As a result of the novel porous wire structure, the wire electrode may further comprise (1) at least one immunoreactive agent selected from a group consisting of cells, whole blood, blood serum, biodegradable polymers sugars, amino acids, proteins, iron, lipopolysaccharides, collagen and hyaluronic acid (2) at least one anti-inflammatory agent selected from a group consisting of steroids, anti-oxidants, superoxide dismutase mimetics and non-steroidal anti-inflammatory drugs, (3) at least one hemostatic agent selected from a group consisting of microfibrillar collagen hemostat, chitosan, kaolin, zeolite, anhydrous aluminum and sulfate, (4) at least one pharmacological agent selected from a group consisting of an antibiotic, an anti-fungal, an analgesic and an anesthetic, and/or a contrast agent for visualization during ultrasound, fluoroscopy or x-ray selected from a group consisting of fluroscein and platinum.

The injectable wire electrode in some embodiments comprises at least two highly conductive wires having different properties selected from the group consisting of diameter, impedance, flexibility, strength, radio-opacity.

To assist in placement of the wire electrode, it may further comprise a guide wire embedded within said wire electrode, and optionally said guide wire may remain in place or be configured to be removed from said wire electrode after placement. Said guide wire may pre-bent or comprise a shape-memory.

Said wire structure electrode, in other embodiments, further comprises a reinforcer intermittently, said reinforcer providing rigidity and being made of materials discussed elsewhere in this disclosure.

l. Wrapped Wire Structure Electrode

Disclosed herein is a wrapped wire structure electrode for injection on or near a tissue target in a body comprising a bulk shape comprising a plurality of highly conductive wires. In one embodiment, said bulk shape comprises a roughened and porous surface, and said bulk shape being configured to be flexible, bendable, stretchable and deformable after injection into the body while maintaining conductivity during normal use in the body. In yet another embodiment, the electrode further comprises a guide wire positioned in a center of said bulk shape. Said electrode, on account of its structure and composition, induces assimilation of the electrode with the surrounding tissues of the body.

m. Twisted or Braided Wire Structure Electrode

Also disclosed is a twisted or braided wire structure electrode for injection on or near a tissue target in a body comprising a bulk shape comprising a plurality of highly conductive wires twisted or braided together, said bulk shape being configured to be flexible, bendable, stretchable and deformable after injection into the body while maintaining conductivity during normal use in the body. An additional embodiment further comprises a guide wire positioned in a center of said bulk shape. Said electrode, on account of its structure and composition, induces assimilation of the electrode with the surrounding tissues of the body.

We claim:

1. An ex vivo method of manufacturing a wire structure electrode for implantation injection near a tissue target inside a body, the method comprising the steps of:
    providing at least one highly conductive wire;
    wrapping the at least one highly conductive wire around at least one mandrel outside the body to produce spools comprising two ends; and
    compacting the spools to form a wire structure not exceeding 3 mm in diameter having voids and a roughened and porous surface, wherein said step of compacting the spools further comprises compacting the spools about a guidewire.

2. An ex vivo method of manufacturing a wire structure electrode for implantation injection near a tissue target inside a body, the method comprising the steps of:
    providing at least one highly conductive wire;
    wrapping the at least one highly conductive wire around at least one mandrel outside the body to produce spools comprising two ends; and
    compacting the spools to form a compacted wire structure not exceeding 3 mm in diameter having voids and a roughened and porous surface, wherein said step of compacting is performed so as to create areas having differing compaction ratios such that the compacted wire structure is configured with varying density along its length.

3. An ex vivo method of manufacturing a wire structure electrode for implantation injection near a tissue target inside a body, the method comprising the steps of:
    providing at least one highly conductive wire;
    wrapping the at least one highly conductive wire around at least one mandrel outside the body to produce spools comprising two ends;
    compacting the spools to form a compacted wire structure not exceeding 3 mm in diameter having voids and a roughened and porous surface; and
    applying a reinforcer to at least one location on the compacted wire structure to create intermittent rigidity along its length.

* * * * *